(12) United States Patent
Zhou et al.

(10) Patent No.: US 7,511,139 B2
(45) Date of Patent: Mar. 31, 2009

(54) PROCESS FOR THE PREPARATION OF ENTECAVIR AND NOVEL INTERMEDIATES THEREOF VIA CARBON-SILICON OXIDATION

(75) Inventors: Maotang X. Zhou, Jamesville, NY (US); Emily A. Reiff, Milltown, NJ (US); Purushotham Vemishetti, Monmouth Junction, NJ (US); Yadagiri R. Pendri, South Glastonbury, CT (US); Ambarish K. Singh, Bordentown, NJ (US); Siva Josyula Prasad, Kendall Park, NJ (US); Ulhas P. Dhokte, Kendall Park, NJ (US); Xinhua Qian, Flemington, NJ (US); Pia Mountford, Barceloneta, PR (US); Kerry B. Hartung, Minoa, NY (US); Helen Sailes, Dublin (IE)

(73) Assignee: Bristol-Myers Squibb Company, Princeton, NJ (US)

( * ) Notice: Subject to any disclaimer, the term of this patent is extended or adjusted under 35 U.S.C. 154(b) by 593 days.

(21) Appl. No.: 11/143,268

(22) Filed: Jun. 2, 2005

(65) Prior Publication Data

US 2005/0272932 A1 Dec. 8, 2005

Related U.S. Application Data

(60) Provisional application No. 60/576,899, filed on Jun. 4, 2004.

(51) Int. Cl.
C07D 473/00 (2006.01)
(52) U.S. Cl. ..................................... 544/264
(58) Field of Classification Search ................ 544/264, 544/265
See application file for complete search history.

(56) References Cited

U.S. PATENT DOCUMENTS

| | | | |
|---|---|---|---|
| 4,471,130 A | 9/1984 | Katsuki et al. | 549/523 |
| 4,594,439 A | 6/1986 | Katsuki et al. | 549/523 |
| 4,900,847 A | 2/1990 | Hanson et al. | 549/529 |
| 5,206,244 A | 4/1993 | Zahler et al. | 514/262 |
| 6,627,224 B2 | 9/2003 | Colonno et al. | 424/480 |
| 2003/0190334 A1 | 10/2003 | Desai et al. | |
| 2004/0192912 A1 | 9/2004 | Pendri et al. | |

FOREIGN PATENT DOCUMENTS

| | | |
|---|---|---|
| WO | WO 98/09964 | 3/1998 |
| WO | WO 03/086367 | 10/2003 |
| WO | WO 2004/052310 | 6/2004 |

OTHER PUBLICATIONS

Bisacchi et al., Bioorganic & Medicinal Chem. Letters, vol. 7, p. 127-132, 1997.
Ziegler et al. Tetrahedron, vol. 59, p. 9013-9018, 2003.
Carceller et al., Tetrahedron Letters, vol. 25, p. 2031-2034, 1984.
Pearson et al., Organic Letters, vol. 5, p. 2457-2459, 2003.
Humiliere et al., Synlett, Nov. 1998, p. 1255-1257.
Bonini et al., Tetrahedron, vol. 58, p. 4981-5021, 2002.
Fleming, Chemtracts—Organic Chemistry, Jan. / Feb. 1996.
Danishefsky et al., J. Am. Chem. Soc., vol. 111, p. 3456-3457, 1989.
Greene et al., Protective Groups in Organic Synthesis, 1991, p. 198-201.
Griffith et al., J. Am. Chem Soc., vol. 118, p. 9526-9538, 1996.
Khanapure et al., J. Org. Chem., vol. 60, p. 7548-7551, 1995.
Li et al., Angew. Chem. Int. Ed. English, vol. 35, p. 2813-2817, 1996.
Jones et al., Tetrahedron, vol. 52, p. 7599-7662, 1996.
Miyaji et al., Tetrahedron Letters, vol. 32, p. 4557-4560, 1991.

Primary Examiner—James O. Wilson
Assistant Examiner—Paul V. Ward
(74) Attorney, Agent, or Firm—James Epperson; Henry H. Gu

(57) ABSTRACT

Processes for preparing entecavir and novel intermediates thereof using carbon-silicon oxidation.

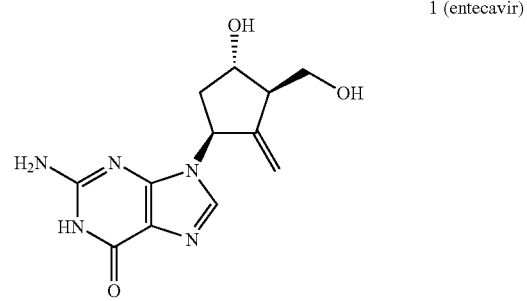

1 (entecavir)

3 Claims, No Drawings

PROCESS FOR THE PREPARATION OF ENTECAVIR AND NOVEL INTERMEDIATES THEREOF VIA CARBON-SILICON OXIDATION

RELATED APPLICATION

This application claims the priority benefit of U.S. Provisional Application No. 60/576,899 filed Jun. 4, 2004, the disclosure of which is incorporated herein by reference in its entirety.

BACKGROUND OF THE INVENTION

Entecavir, [1S-(1α,3α,4β)]-2-amino-1,9-dihydro-9-[4-hydroxy-3-(hydroxymethyl)-2-methylenecyclopentyl]-6H-purin-6-one monohydrate, is currently being used as a drug for treating hepatitis B viral infections.

Entecavir and its use as an antiviral agent are described by Zahler et al. in U.S. Pat. No. 5,206,244. Improved processes of preparing entecavir are described by Bisacchi et al., in WO 98/09964, and by Pendri et al., in WO2004/052310 and US20040192912. The disclosure of each of the foregoing patent or patent applications is herein incorporated by reference in its entirety.

Colonno et al. in WO 01/64221 describe compositions containing a low dose of entecavir administered on a daily basis to treat hepatitis B virus infection and/or co-infections.

The discussion of the background to the invention herein is included to explain the context of the invention This is not to be taken as an admission that any of the material referred to was prior art as at the priority date of any of the claims.

SUMMARY OF THE INVENTION

This invention is directed to various methods for preparing entecavir as recited in the claims appended hereto. Entecavir is the monohydrate of the compound of formula I, which has the structural formula shown below:

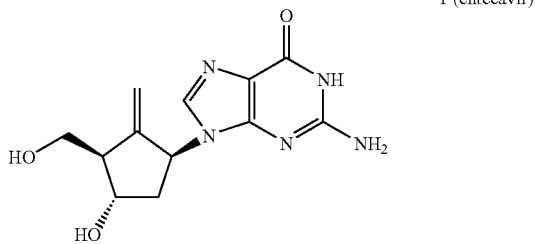

1 (entecavir)

This invention is also directed to various intermediates useful in the preparation of entecavir and the methods of preparing such intermediates.

DETAILED DESCRIPTION OF THE INVENTION

Abbreviations

For ease of reference, the following abbreviations are used in this application and have the meanings given below:
AcOH acetic acid
$Ac_2O$ acetic anhydride
AP HPLC area percent
Bn benzyl
BnBr benzyl bromide
BHT 2,6-di-tert-butyl-4-methylphenol
CHP cumene hydroperoxide, or α,α-dimethylbenzylhydroperoxide
CSA (1R)-(−)-camphorsulfonic acid
DCM dichloromethane
DDQ 2,3-dichloro-5,6-dicyano-1,4-benzoquinone
(−)-DIPT diisopropyl D-tartrate
DMF N,N-dimethylformamide
DMSO dimethyl sulfoxide or methyl sulfoxide
EtOAc ethyl acetate
FMSA fluoromethane sulfonic acid
KHMDS potassium hexamethyldisilazide or potassium bis(trimethylsilyl)amide
KOtBu potassium tert-butoxide
MCPBA meta-chloroperbenzoic acid
MSA methanesulfonic acid
NMP 1-methyl-2-pyrrolidinone
PMB para-methoxybenzyl
PMBCl para-methoxybenzyl chloride
PPTS pyridinium 4-toluenesulfonate
PTSA para-toluene sulfonic acid
RAP relative area percent
TBAF tetrabutylammonium fluoride
TBAHS tetrabutylammonium hydrogensulfate
TBHP tert-butyl hydroperoxide
TFA trifluoroacetic acid
THF tetrahydrofuran
TFMSA trifluoromethanesulfonic acid
$Ti(OiPr)_4$ titanium isopropoxide
TIOF triisopropyl orthoformate

Definitions

The following terms shall have, for the purposes of this application, including the claims appended hereto, the respective meanings set forth below. It should be understood that when reference herein is made to a general term, such as acid, base, oxidizing agent, etc. one skilled in the field may make appropriate selections for such reagents from those given in the definitions below, as well as from additional reagents recited in the specification that follows, or from those found in literature references in the field.

"Anhydride" refers generally to compounds that will react with water or solvent to form an acid, e.g., including carboxylic acid anhydrides having the formula R—C(=O)—O—C(=O)R', wherein R and R' are selected from alkyl or aryl groups, as defined below, more preferably, wherein R and R' are selected from methyl and ethyl.

"Acid" refers to any compound that contains hydrogen and dissociates in water or solvent to produce positive hydrogen ions, as well as Lewis acids, including but not limited to acids such as hydrochloric acid, sulfuric acid, phosphoric acid, acetic acid, trihaloacetic acid (e.g., TFA), hydrogen bromide, maleic acid, sulfonic acids such as toluenesulfonic acids and camphorsulfonic acids, propionic acids such as (R)-chloropropionic acid, phthalamic acids such as N—[(R)-1-(1-naphthyl) ethyl]phthalamic acid, tartaric acids such as L-tartaric acid and dibenzyl-L-tartaric acid, lactic acids, camphoric acids, aspartic acids, citronellic acids, $BCl_3$, $BBr_3$, and so forth. Thus, the term includes weak acids such as ethanoic acid and hydrogen sulfide; strong organic acids such as methanesulfonic acid, trifluoroacetic acid, and so forth.

"Alkyl" as used herein includes linear or branched alkyl groups having from one to twelve carbon atoms, more preferably from one to eight carbon atoms, and most preferably, from one to four carbon atoms, unless otherwise specifically described. The term alkyl includes such groups optionally having up to four (more preferably 0 to 2), substituents selected from the group of non-interfering substituents recited below. The term lower alkyl refers to alkyl groups having from one to four carbon atoms. When a subscript is used with reference to an alkyl or other group, the subscript refers to the number of carbon atoms that the group may contain. For example, the term "$C_1$-$C_4$ alkyl" refers to alkyl groups of 1 to 4 carbon atoms, which include methyl, ethyl, propyl, isopropyl, n-butyl, isobutyl, and t-butyl. Alkyl moieties incorporated in other radicals are also linear or branched, unless specifically described otherwise. When the term alkyl is used as a prefix in conjunction with another group, as in alkylaryl, this means the alkyl as defined above is present as a divalent moiety (i.e., alkylene), creating a linkage to the other named group. Thus, alkylaryl includes benzyl and the like.

"Alkoxy" as used herein includes alkyl groups as defined above, bonded through an oxygen atom, i.e., —O-alkyl. "$C_1$-$C_4$ alkoxy" refers to —O—$C_1$-$C_4$ alkyl.

"Alkali metal salt" refers to salts formed with alkali metals, preferably salts of sodium, lithium or potassium.

"Allyl" refers to the group —$CH_2$—CH=$CH_2$, as well as such groups optionally having one or more (preferably 0 to 1) non-interfering substituents as defined below.

"Anti-oxidant" refers to a chemical compound or complex that is effective to slow or inhibit the rate of an oxidation reaction. Exemplary anti-oxidants may include, without limitation, β-carotene, $ZrO_2$, aromatic amines, phenols, quinones including BHT, citric acid, ascorbic acid, vitamin E, benzoic acid, phosphoric acid, and so forth.

"Aryl" includes monocyclic or bicyclic aromatic groups having 6 to 12 carbon atoms in the ring portion, i.e., phenyl and naphthyl, as well as heteroaryl groups, e.g., 4 to 7 membered monocyclic, 7 to 11 membered bicyclic, or 10 to 15 membered tricyclic aromatic ring systems, which have at least one heteroatom and at least one carbon atom-containing ring. Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like. Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, and the like. The term "aryl" includes aryl groups optionally having up to four (preferably 0 to 2) non-interfering substituents.

"Base" when used herein includes hydroxides or alkoxides, hydrides, or compounds such as amine and its derivatives, that accept protons in water or solvent. Thus, exemplary bases include, but are not limited to, alkali metal hydroxides and alkoxides (i.e., MOR, wherein M is an alkali metal such as potassium, lithium, or sodium, and R is hydrogen or alkyl, as defined above, more preferably where R is straight or branched chain $C_{1-5}$ alkyl, thus including, without limitation, potassium hydroxide, potassium tert-butoxide, potassium tert-pentoxide, sodium hydroxide, sodium tert-butoxide, lithium hydroxide, etc.); other hydroxides such as magnesium hydroxide ($Mg(OH)_2$) or calcium hydroxide ($Ca(OH)_2$), barium hydroxide ($Ba(OH)_2$); alkali metal hydrides (i.e., MH, wherein M is as defined above, thus including, without limitation, sodium, potassium, and lithium hydrides); alkylated disilazides, such as, for example, potassium hexamethyldisilazide and lithium hexamethyldisilazide; carbonates such as potassium carbonate ($K_2CO_3$), sodium carbonate ($Na_2CO_3$), potassium bicarbonate ($KHCO_3$), and sodium bicarbonate ($NaHCO_3$), alkyl ammonium hydroxides such as tetrabutyl ammonium hydroxide (TBAH) and so forth. Aqueous bases include metal hydroxides, for example, hydroxides of Group 1/Group 2 metals such as Li, Na, K, Mg, Ca, etc. (e.g., aqueous LiOH, NaOH, KOH, etc.), alkyl ammonium hydroxides, and aqueous carbonates. Non-aqueous bases include but not limited to, amines and their derivatives, for example, trialkyl amine (e.g., $Et_3N$, diisopropylethyl amine, etc.), and aromatic amine (e.g., Ph-$NH_2$, PhN(Me)H, etc.); alkali metal alkoxides; alkali metal hydrides; alkylated disilazides; and non-aqueous carbonates.

"Benzyl" includes the group —$CH_2$-phenyl, as well as such groups optionally containing non-interfering substituents on the methyl or phenyl portions of the benzyl, unless otherwise indicated.

"Benzyl halide" refers to a benzyl group having a halide substituent on the alkyl portion of the benzyl group, i.e., Ph-$CH_2$—X, wherein X is halide, and Ph denotes a phenyl ring as defined below.

"Benzyloxy" refers to the group —O-benzyl, wherein the benzyl moiety is as described immediately above.

"Diastereoselective epoxidation" refers to a reaction wherein one diastereomeric epoxide is preferentially formed. The term "diastereoselective epoxidation" thus includes Sharpless epoxidations wherein epoxidation of an allylic alcohol preferentially gives one enantiomer. However, the term "diastereoselective epoxidation" as used herein also more broadly covers the epoxidation of a diastereomeric compound, or the epoxidation of an otherwise non-racemic compound. The term "diastereoselective epoxidation" is intended to include enantioselective oxidation of olefins as described in Bonini and Righi, "A Critical Outlook And Comparison of Enantioselective Oxidation Methodologies of Olefins", Tetrahedron, Vol. 58 (2002), at pp. 4981-5021, incorporated herein by reference.

"Halide" or "halo" refers to F, Cl, Br, or I.

"Halogenated methanesulfonic acid" refers to methanesulfonic acid substituted with one, two or three halogens, for example, monofluromethanesulfonic acid, difluromethanesulfonic acid, trifluromethanesulfonic acid, monochloromethanesulfonic acid, dichloromethanesulfonic acid, trichloromethanesulfonic acid, monobromomethanesulfonic acid, dibromomethanesulfonic acid, tribromomethanesulfonic acid, monoiodomethanesulfonic acid, and diiodomethanesulfonic acid.

"Hydride reagent" refers to reagents that are capable of delivering $H^-$ ions. Exemplary hydride reagents include, but are not limited to, lithium aluminum hydride (LiAlH4), sodium borohydride ($NaBH_4$), Red-Al® (sodium bis[2-methoxyethoxyaluminum]hydride), zinc borohydride, diisobutylaluminum hydride, sodium borohydride-cerium chloride, lithium triethylborohydride, lithium 9-BBN hydride, 9-BBN pyridine, borane-sulfide complex, 5,5-diphenyl-2-methyl-3,4-propan-1,3,2-oxazaborolidine (Corey Reagent), lithium tri-tert-butoxyaluminum hydride, sodium cyanoborohydride, lithium tri-sec-butyl borohydride (L-Selectride®), diisobutylaluminum chloride, borane-tetrahydrofuran complex, and the like.

"Hydroperoxide" means a compound or complex comprising the hydroperoxide moiety $HO_2^-$, such as compounds having the formula ($R^POOH$), wherein $R^P$ can be hydrogen (e.g., hydrogen peroxide $H_2O_2$), or can be an alkyl, substituted alkyl, aryl, alkylaryl, substituted aryl, or substituted alkylaryl or other moiety (including without limitation compounds wherein the methyl moiety of the benzyl group is optionally substituted). Hydroperoxides thus include α,α-dimethylbenzylhydroperoxide, tert-butylhydroperoxide, and the like.

"Hydroxy protecting groups" means those groups that one skilled in the field would recognize as being suitable to protect the —OH substituent on an alkyl or ringed system as described herein and which may be removed under deprotection conditions known to those skilled in the field as set forth, for example, in the latest edition of Greene and Wuts, Protecting Groups in Organic Synthesis, incorporated herein. As an illustration, nonlimiting examples of hydroxy protecting groups include ether protecting groups (e.g. benzyl ethers, silyl ethers such as tert-butyldimethylsilyl ether), esters (e.g., benzoate, acetate), and acetals (e.g., MOP).

"Homochiral diester of tartaric acid" as used herein includes single diastereomers of alkyl tartrates including diethyl tartrate and diisopropyl tartrate.

"Metal catalyst" refers to compounds and complexes including metallic elements that are effective as catalysts and encompasses, without limitation, "transition metal catalysts." Metal catalysts include, without limitation, titanium (IV) isopropoxide, palladium salts such as palladium (0) catalyst, e.g., tetrakis(triphenylphosphine)palladium, copper(I)triflate, rhodium(II) acetate, $Rh_6(CO)_{16}$, and so forth.

"Non-interfering substituent" refers to a substituent that is bonded to a compound or complex identified herein that does not render the compound or complex inoperable, with regard to the functionality or object to be achieved with the particular compound or complex, and which is compatible with the reaction sequences detailed herein. Such substituents may be selected by one skilled in the field depending on the particular reaction step and function to be achieved. Exemplary non-interfering substituents may include without limitation groups such as alkyl, halogen, cyano, nitro, trifluoromethyl, trifluoromethoxy, —OR, —SR, —C(=O)R, —$CO_2$R, aryl, alkylaryl, $C_{3-7}$cycloalkyl, —NRR'$_2$, —NRC(=O)R', —$SO_{(q)}$R", —NRS$O_{(q)}$R", —S$O_{(q)}$R", —C(=O)NRR', and the like; and alkyl groups substituted with one to four (preferably 1 to 2) of halogen, cyano, nitro, trifluoromethyl, trifluoromethoxy, —OR, —SR, —C(=O)R, —$CO_2$R, aryl, alkylaryl, $C_{3-7}$cycloalkyl, —NRR'$_2$, —NR—C(=O)R', —$SO_{(q)}$R", —NRS$O_{(q)}$R", —S$O_{(q)}$R", —C(=O)NRR', and the like, wherein R and R' are hydrogen, alkyl, benzyl, or aryl, as defined above, R" is alkyl, benzyl, or aryl, as defined above, and q is 1, 2 or 3.

"Orthoformate derivatives" means reagents effective for the preparation of dioxolanes from vicinal diol moieties, or for the preparation of imidazole rings from vicinal diamines on, for example 5,6-diaminopyrimidine derivatives. Non-limiting examples include triethylorthoformate, trimethylorthoformate, triisopropylorthoformate, diethoxymethyl acetate, and di-isopropyloxymethylacetate.

"Oxidizing agent," or "oxidizing source" refers to any compound or complex that is known in the field for its effects in converting a functional group in a molecule from a lower oxidation state to a higher oxidation state. For example, oxidizing agents may include, without limitation, m-CPBA, hydrogen peroxide, AcOOH in AcOH, potassium peroxymonosulfate, sodium periodate, sodium percarbonate, potassium permanganate, ruthenium oxide, and the like. Oxidizing agents may be used in the presence of one or more additives, such as KF, $KHCO_3$, $NEt_3$, AcONa, and the like. As one skilled in the field will appreciate, additives may be selected depending on the particular oxidizing agents used and the reaction conditions.

"Per-acid" as used herein includes without limitation, magnesium monoperoxyphthalate (MPPA), perbenzoic acids, and peracetic acid.

"Peroxohydrates" are crystalline adducts containing molecular hydrogen peroxide, for example, sodium carbonate peroxohydrate (known commercially as sodium percarbonate, e.g., $Na_2CO_3.1.5\ H_2O_2$), urea peroxohydrate ($CO(NH_2)_2.H_2O_2$), the peroxohydrate of melamine, ($C_3H_6N_6.H_2O_2$), sodium pyrophosphate peroxohydrate ($Na_4P_2O_7.2\ H_2O_2$), sodium sulfate peroxohydrate hydrate ($2\ Na_2SO_4.H_2\ O_2.2H_2O$), potassium carbonate peroxohydrates, rubidium carbonate peroxohydrates, and cesium carbonate peroxohydrates (the last three have the general formula $M_2CO_3.3H_2O_2$).

"Phenyl" includes phenyl rings optionally substituted with up to four (preferably 0 to 2) non-interfering substituents as defined above. When the term phenyl is used as a suffix following another term, as in alkylphenyl, or alkoxy phenyl, this means the phenyl group is connected via a divalent moiety of the other, specifically-named group. Thus, alkylphenyl includes benzyl, phenylethyl, and the like.

"Protecting group" includes without limitation such groups as are set forth, for example, in the latest edition of Greene and Wuts, Protecting Groups in Organic Synthesis, incorporated herein by reference.

"Reducing reagent" refers to any compound or complex that is known in the field for its effects in converting a functional group in a molecule from one oxidation state to a lower oxidation state. Exemplary reducing reagents include, without limitation, $NaBH_4$, LAH, lithium borohydride, diisobutylaluminum hydride, sodium bis(2-methoxyethoxyaluminum)hydride, and the like. The term "reducing reagent" will include "hydride reagents" as recited above.

"Strong non-nucleophilic base" means a non-aqueous base that does not act as a nucleophile, such as lithium, sodium or potassium bistrimethylsilylamide, lithium diisopropylamide, potassium, lithium, or sodium hydride.

"Tertiary amine base" means a trialkylamine, such as triethylamine, N,N-dimethylethylamine, diisopropylethylamine (Hunig's base) or tetramethylenediamine (TMEDA), or a nitrogen containing heterocycle, such as pyridine.

"Trimethylsilylating reagent" means a reagent effective to prepare a trimethylsilyl ether from an alcohol. Non-limiting examples include chlorotrimethylsilane, trimethylsilyl trifluoromethanesulfonate, and the like.

Additionally, it should be understood in the methods of preparation and claims herein, that the pronoun "a", when used to refer to a reagent, such "a base", "a metal catalyst", "a hydroperoxide" and so forth, is intended to mean "at least one" and thus, include, where suitable, single reagents as well as mixtures of reagents. Thus, for example, a reaction step involving use of "a base", or for example, involving use of "a base selected from one of potassium hydroxide, potassium tert-butoxide, potassium tert-pentoxide, sodium hydroxide, sodium tert-butoxide, lithium hydroxide," encompasses use of potassium hydroxide as a base, or, where appropriate, mixtures of potassium hydroxide plus one or more additional bases set forth in the group from which a selection may be made. One skilled in the field may make appropriate selections given the reactions steps and conditions and result to be achieved.

Methods of Preparation

The compound entecavir and novel intermediates therefore may be prepared by the exemplary processes described in the following reaction Schemes. Exemplary reagents and procedures for these reactions appear hereinafter or are described above. Starting materials can be readily prepared according to methods described in WO2004/052310 and US20040192912. Solvents, temperatures, pressures, starting materials having the desired groups, and other reaction conditions, may be readily selected as appropriate by one of ordinary skill in the art.

The compound of formula I (entecavir) can be prepared from an alcohol of formula 1a according to Scheme 1. In the alcohol of formula 1a, $R^a$ is allyl, phenyl, or phenyl substituted with one, two or three $C_1$-$C_4$ alkyl or $C_1$-$C_4$ alkoxy, preferably $R^a$ is phenyl; and each $R^b$ is independently $C_1$-$C_4$ alkyl, preferably methyl. The definitions of $R^a$ and $R^b$ are the same as hereinabove throughout the specification, unless otherwise indicated. The primary alcohol moiety of the compound of formula 1a is protected with a PMB protecting group by treatment with PMB-halide (e.g., PMB-Cl), and in the presence of a base and optionally a catalyst (e.g., TBAHS), in an organic solvent such as toluene, to yield a compound of formula 1b. The compound of formula 1b can be converted to a compound of formula 1c via protodesilylation. The protodesilylation step can be achieved via reaction with boron trifluoride-acetic acid complex, or a Brønsted acid such as TFA, MSA, FMSA, or tetrafluoroboric acid in an inert solvent, e.g., DCM. Alternatively, protodesilylation can be achieved with a base (e.g., a hydroxide such as NaOH or KOH, an alkoxide such as KOtBu) or a strong acid (e.g., TFA), in a polar aprotic solvent such as DMF, DMSO, or NMP, to give the compound of formula 1c. The compound of formula 1c is further oxidized using an oxidizing reagent, for example, $H_2O_2$, in the presence of KF and $KHCO_3$ to afford an alcohol of formula 1d. In addition, other methods may also be useful in the transformation of the silyl group to the hydroxyl group, see, e.g., Fleming, I. (*Chemtracts-Organic Chemistry* 1996, 9, 1-64) and Jones, G. R. et al. (*Tetrahedron*, 1996, 52, 7599-7662), both of which are herein incorporated by reference.

The alcohol of formula 1d is protected as a benzyl ether of formula 1e using a benzyl halide, such as BnBr, in the presence of a base, such as KHMDS or NaH, and in an organic solvent, such as toluene. The PMB group in the compound of formula 1e can be removed upon treatment with DDQ in an organic solvent such as $CH_2Cl_2$ in the presence of water to yield a compound of formula 1f.

The compound of formula 1f can then be diastereoselectively epoxidized. For example, the epoxidation can be accomplished using a homochiral diester of tartaric acid, a hydroperoxide, and a metal catalyst, such as a transition metal catalyst, to yield a cyclopentane epoxide of formula 1g. In one embodiment, the homochiral diester is (−)-diisopropyl tartrate [(−)-DIPT], the hydroperoxide is TBHP or CHP, and the metal catalyst is titanium (IV) isopropoxide. Preferably, the reaction is carried out in an inert solvent such as DCM or toluene.

The epoxide of formula 1g can be subsequently coupled to an alkali metal salt (e.g., lithium) of a purine compound of formula 1h, wherein Y is Cl, Br, I or BnO, in a dipolar aprotic solvent such as DMF to afford a compound of formula 1i. The compound of formula 1h can be prepared according to methods disclosed by Igi et al., in EP 543095 (1993), and by Lolli et al., in J. Labelled Compounds & Radiopharmaceuticals, 41(3), 243-252 (1998). Preferably the coupling of the cyclopentane epoxide of the formula 1g is conducted with the lithium salt of 2-amino-6-benzyloxypurine. The compound of formula 1i, wherein Y is benzyloxy, can be purified by crystallization from solvents such as ethyl acetate and hexanes.

The vicinal diol moiety of the compound of formula 1i can then be converted to an alkene moiety. In one embodiment, the compound of formula 1i can be treated with an orthoformate derivative, e.g, trimethyl orthoformate, in the presence of a catalytic amount of an acid such as TFA or PTSA, or acid catalyst such as PPTS. The resulting mixture of dioxolanes (preferably as a crude mixture) is heated with a mixture of acetic anhydride and optionally acetic acid to provide a methylene compound of formula 1j. Alternatively, this reaction can be performed in the presence of antioxidant such as BHT.

A compound of 1k can be prepared from the compound of formula 1j via hydrolysis. In one embodiment wherein Y is OBn, the 6-O-benzyloxy group can be hydrolyzed (as well as any pendant 2-acetamide group formed from the acetylation of the 2-amino group of the purine during the acetic anhydride treatment step) by heating the compound of formula 1j with aqueous mineral acid, such as 2 N HCl to give the methylene compound of formula 1k. In another embodiment wherein Y is Cl, Br or I, the 6-halo group can be hydrolyzed by treatment with aqueous base (e.g., aqueous hydroxide solution). Finally, removal of the remaining benzyl ether protecting group in the compound of formula 1k upon treatment with a Lewis acid such as $BCl_3$, $BBr_3$, etc., or a Brønsted acid such as MSA, TFMSA, etc., in an inert solvent such as DCM, provides the compound of formula I.

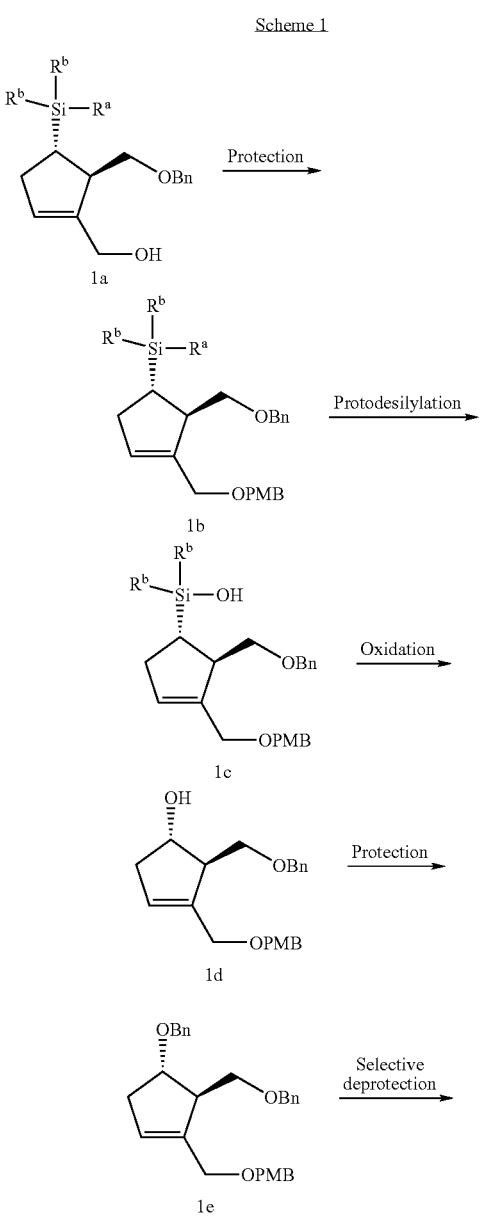

Scheme 1

Alternative syntheses of the compound of formula I are described in Schemes 2 and 3. In Scheme 2, the compound of formula 1c can also be converted to a compound of formula 2a upon treatment with a silylating reagent $R^aSi(R^b)_2$-halide, wherein said silylating reagent is preferably phenyldimethylchlorosilane, in presence of a base, such as imidazole. Deprotection of the PMB group in the compound of formula 2a can be achieved using DDQ in an organic solvent such as $CH_2Cl_2$ in the presence of water to yield an allylic alcohol of formula 2b, which can be converted to a compound of formula 2c via epoxidation as described in Scheme 1. Coupling of the compound of formula 2c with a compound of formula 1h, wherein Y is defined as above, in the presence of an alkali metal base (e.g., LiOH), and in a dipolar aprotic solvent such as DMF, provides a compound of formula 2d, which can be subsequently transformed to a compound of formula 2e through desilylation, which can be achieved with a base such as KOtBu, in a polar aprotic solvent such as DMSO.

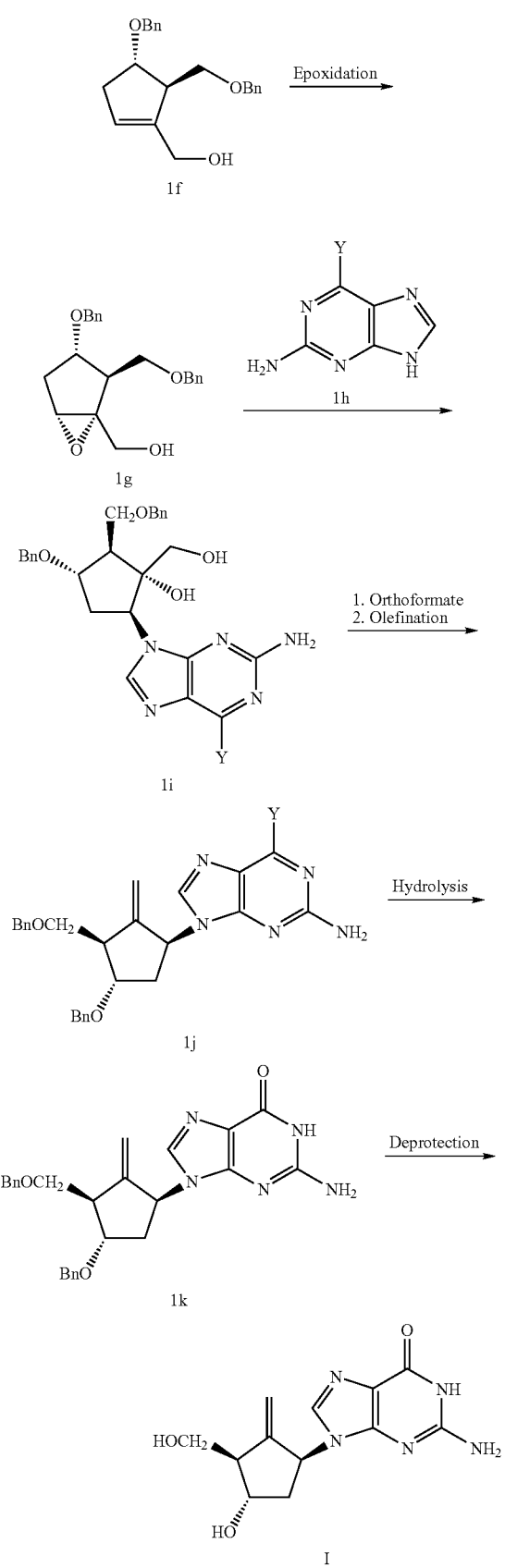

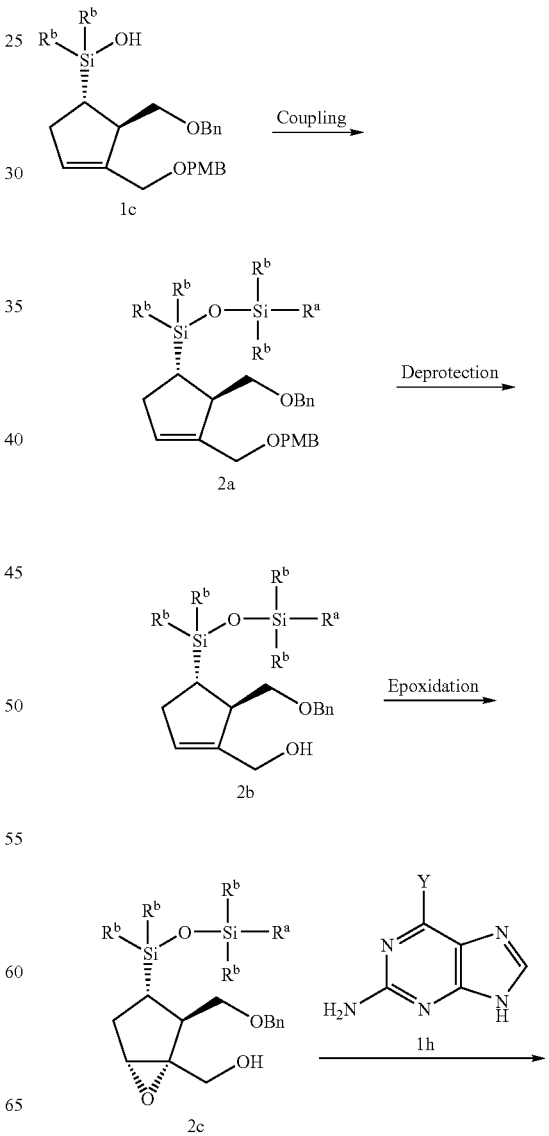

Scheme 2

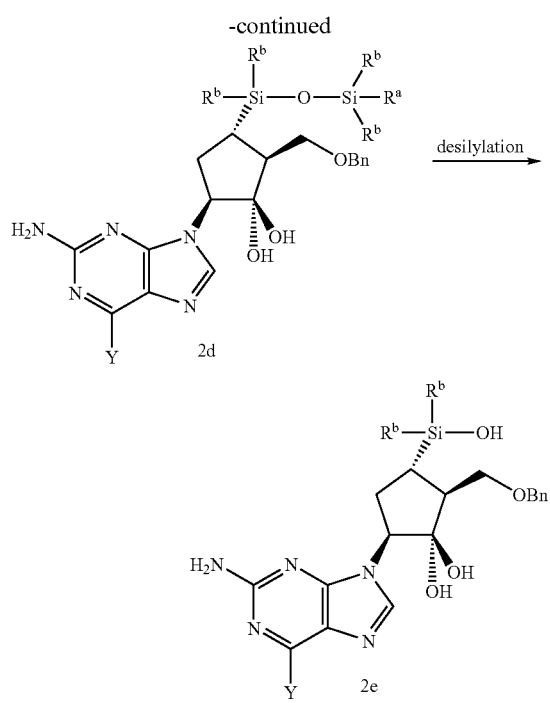

As shown in Scheme 3, the compound of formula I can also be prepared from a compound of formula 3a, which is disclosed as compounds of formula 78A and 73 in WO 2004/052310. A compound of formula 3b can be prepared from the compound of formula 3a via protodesilylation as described in Scheme 1. The compound of formula 3b can be further converted to a mixture of a compound of formula 3c and a compound of formula 3d upon treatment with an orthoformate derivative, e.g, trimethyl orthoformate, in the presence of a catalytic amount of an acid such as TFA or PTSA, or an acid catalyst such as PPTS. The next olefination step was achieved by treating the resulting mixture of compounds 3c and 3d with an acid anhydride having a formula of $R^d$—C(=O)—O—C(=O)—$R^d$, wherein $R^d$ is $C_1$-$C_4$ alkyl preferably methyl; and optionally an acid having a formula of $R^d$—C(=O)OH, wherein $R^d$ is $C_1$-$C_4$ alkyl, preferably methyl; and preferably in the presence of an antioxidant such as BHT, to yield a compound of formula 3e. The definition of $R^d$ is the same as hereinabove throughout the specification, unless otherwise indicated. Hydrolysis of the compound of formula 3e with an aqueous mineral acid, such as 6M HCl, in an organic solvent, such as MeOH, provides a compound of formula 3f. Subsequent oxidation of the compound of formula 3f using the method as described in Scheme 1 affords the compound of formula I (entecavir) when $R^c$ is H; or a compound of formula 3g when $R^c$ is Bn, which can be converted to the compound of formula I (entecavir) by removing the OBn protecting group using the method as described in Scheme 1.

Scheme 3

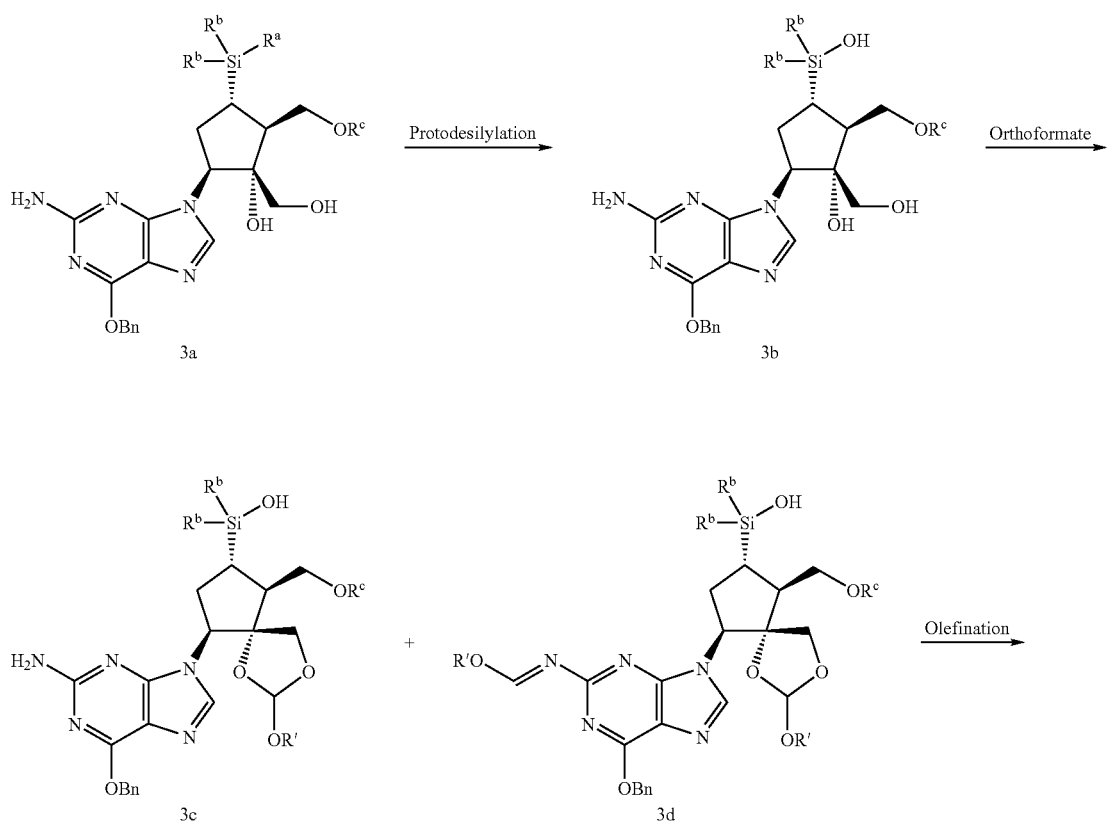

-continued

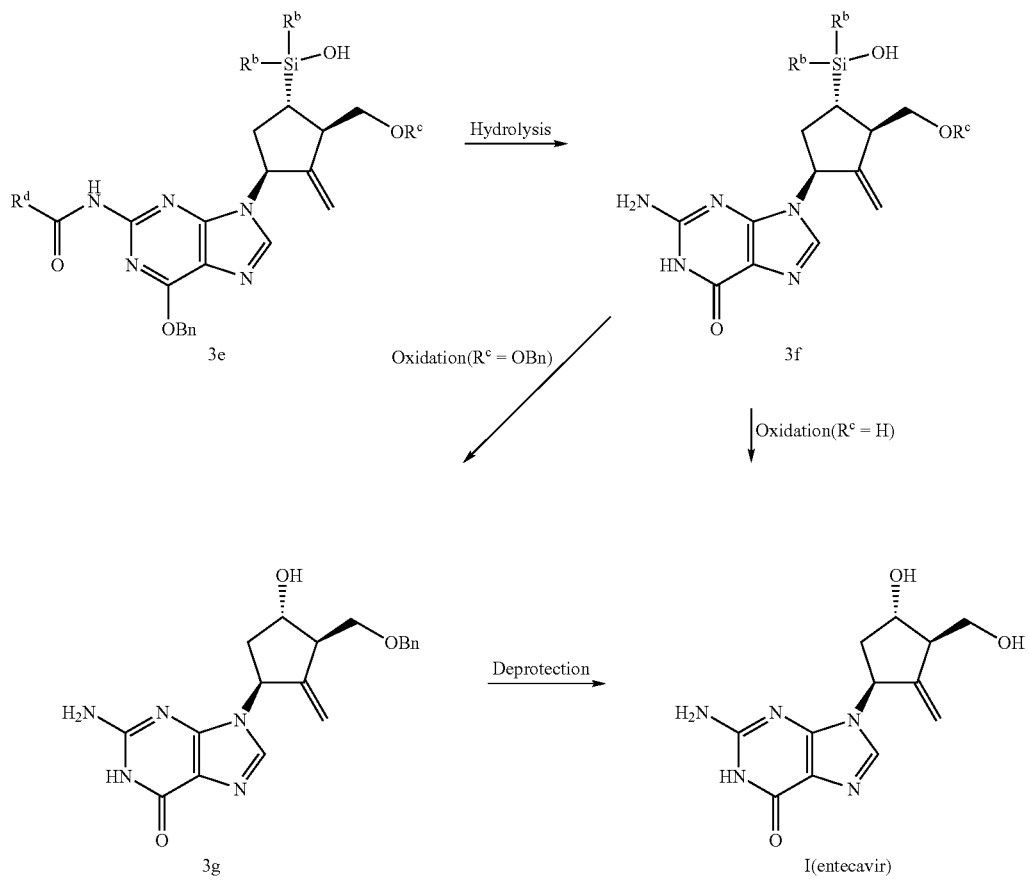

Similarly, the compound of formula I can be prepared from a compound of formula 4a, wherein X is Cl, Br, or I (iodo), in accordance with Scheme 4. The compound of formula 4a is disclosed as compounds of formula 78B and 73 in WO 2004/052310. The transformation from the compound of formula 4a to a compound of 4f is analogous to the method described in Scheme 3. A compound of formula 4g can be obtained from the compound of formula 4f via oxidation using the method as described in Scheme 1. Hydrolysis of the compound of formula 4g upon treatment with an aqueous base provides the compound of formula I (entecavir) when $R^c$ is H; or a compound of formula 4h when $R^c$ is Bn, which can be further converted to the compound of formula I by removing the benzyl group as described in Scheme 1.

Scheme 4

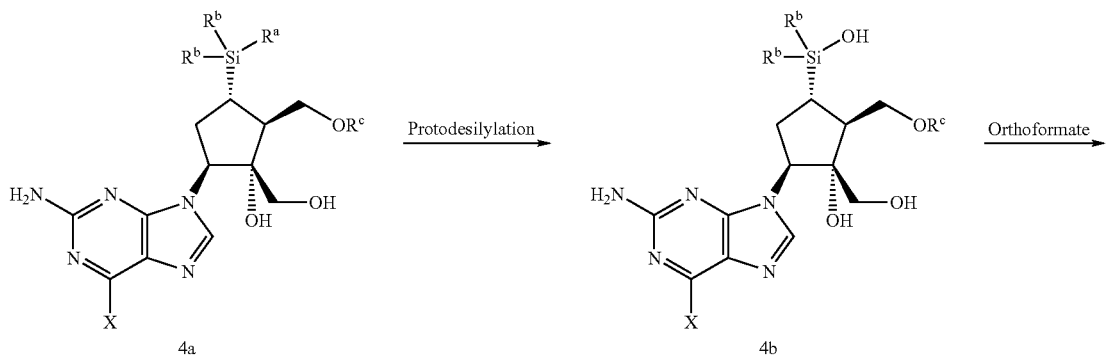

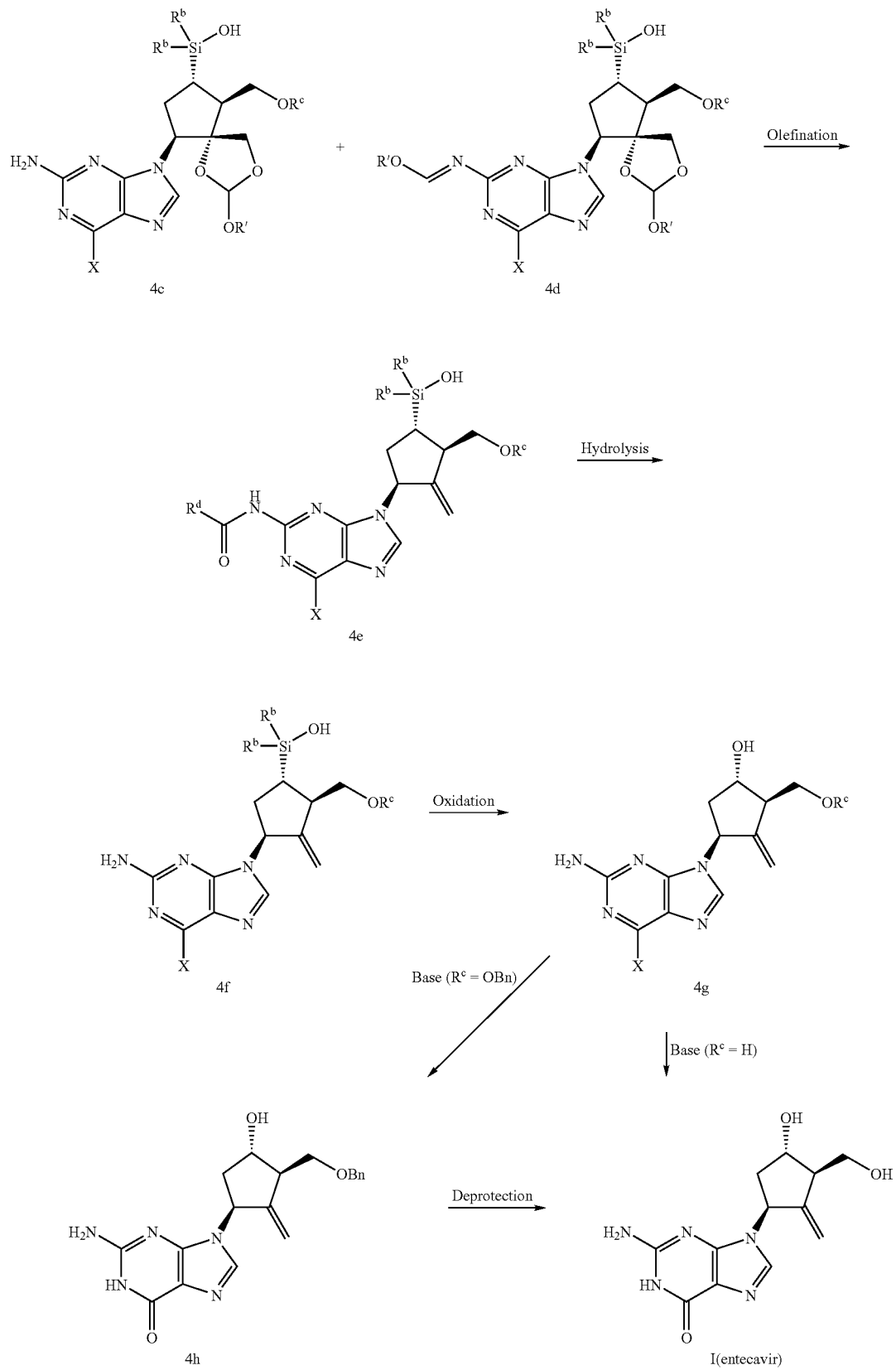

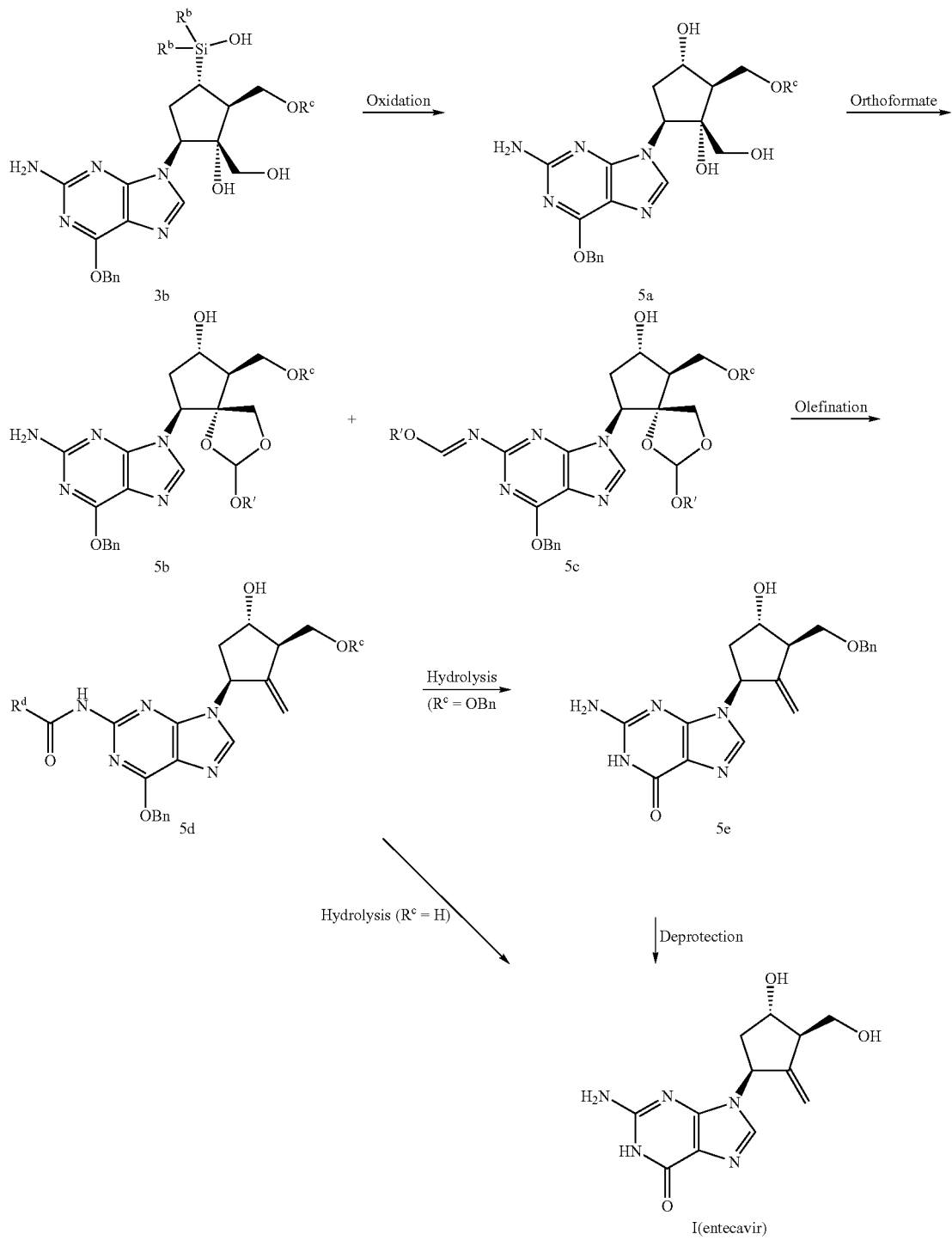

Scheme 5 describes an alternative synthesis of entecavir from the compound of formula 3b. A compound of formula 5a can be obtained from the compound 3b via the oxidation method as described in Scheme 1. A compound of formula 5d can be prepared from the compound of formula 5a via the steps of orthoformate and olefination as described above. Subsequent hydrolysis of the compound of formula 5d with an aqueous mineral acid, such as 6M HCl, in an organic solvent, such as MeOH, provides the compound of formula I (entecavir) when $R^c$ is H; or a compound of formula 5e when $R^c$ is Bn, which can be converted to the compound of formula I (entecavir) via deprotection as described above.

Similarly, the compound of formula I can be prepared from a compound of formula 4b, wherein X is Cl, Br, or I (iodo), in accordance with Scheme 6. The transformation from the compound of formula 4b to a compound of 6d is analogous to the method described in Scheme 5. Hydrolysis of the compound of formula 6d upon treatment with an aqueous mineral acid, such as 6M HCl, in an organic solvent, such as MeOH, affords a compound of formula 6e. Treating the compound of formula 6e with an aqueous base provides the compound of formula I (entecavir) when $R^c$ is H; or the compound of formula 5e when $R^c$ is Bn, which can be further converted to the compound of formula I by removing the benzyl group as described in Scheme 1.

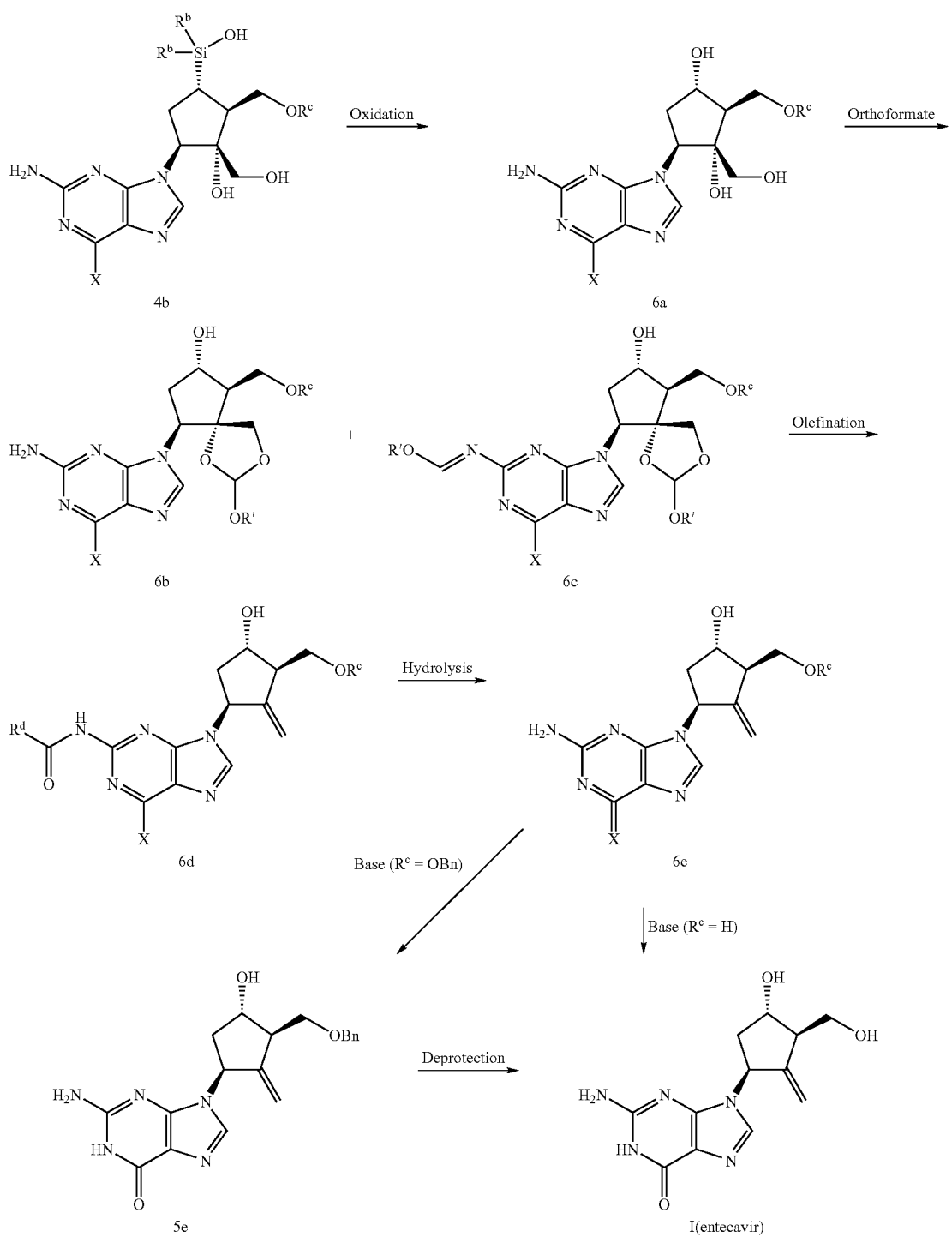

Scheme 7

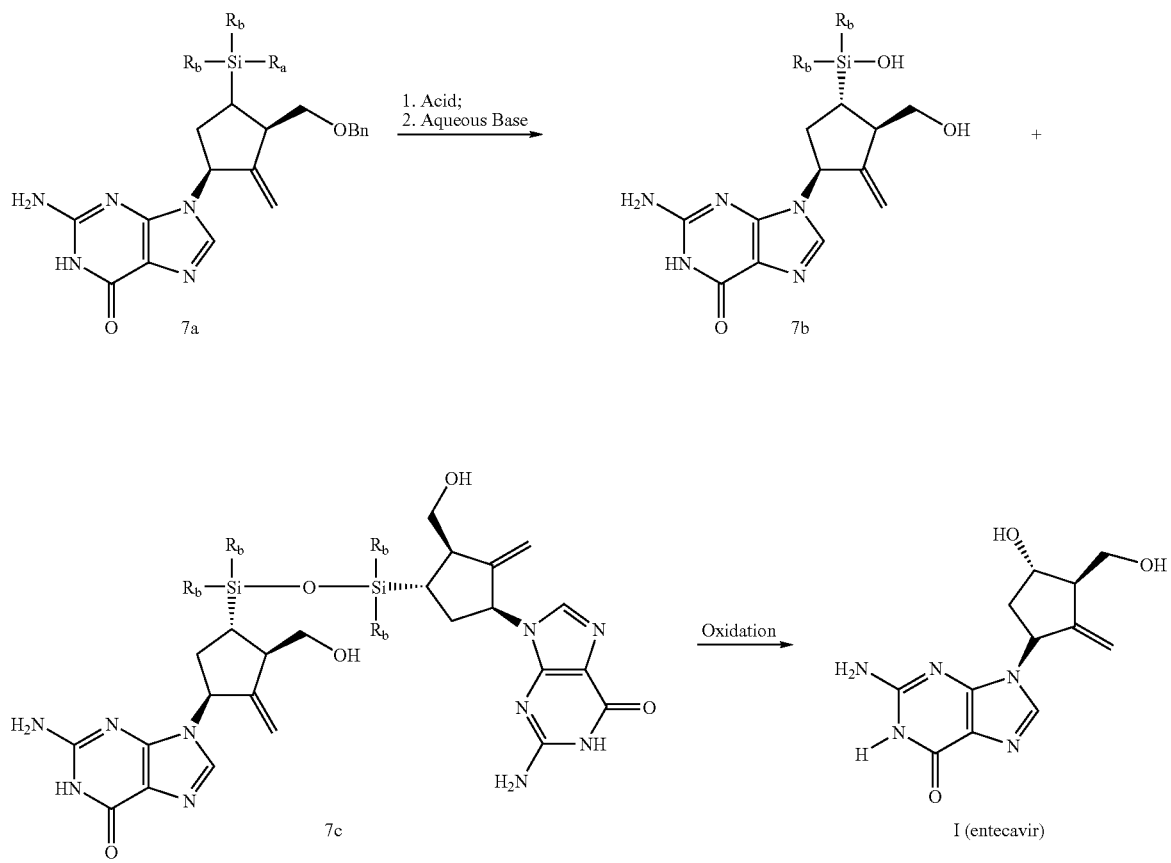

Scheme 7 further describes the synthesis of the compound of formula I from compound 7a, which can be prepared according to a procedure reported by Pendri et al in WO 2004/052310. Treatment of compound 7a with at least one acid selected from: (i) halogenated methanesulfonic acids; and (ii) optionally methanesulfonic acid; preferably a mixture of acids such as trifluoromethanesulfonic acid/methanesulfonic acid, or monofluromethanesulfonic acid/methanesulfonic acid; followed by treatment with at least one aqueous base (e.g., LiOH, NaOH, KOH, etc.) to provide the compound of formula 7b as the major product (typically about 85% to about 95% yield). The compound of formula 7c (dimer of compound 7b) may also be produced and may account for about 5% to about 15% of the total yield (for example, 9.5% and 14.5%).

When a halogenated methanesulfonic acid alone is used, the amount can be less than about 20 mole equivalent, based on 1 mole equivalent of the compound 7a used. For example, the amount of said halogenated methanesulfonic acid can be less than about 10 mole equivalent (e.g., 6 equivalent of monofluromethanesulfonic acid), based on 1 mole equivalent of the compound 7a used. When a mixture of acids such as methanesulfonic acid/trifluoromethanesulfonic acid is used, the amount of said methanesulfonic acid can be less than about 10 mole equivalent and said trifluromethanesulfonic acid can be less than about 10 mole equivalent, based on 1 mole equivalent of the compound 7a used. For example, the amount of said methanesulfonic acid can be less than about 7 mole equivalent (e.g., about 1 to about 7 equivalent, or about 1.5 to about 6.7 equivalent, or about 2 equivalent) and said trifluromethanesulfonic acid can be less than about 5 mole equivalent (e.g., about 1 to about 5 equivalent, or about 2.5 to about 3.5 equivalent), based on 1 mole equivalent of the compound 7a used.

Oxidation of compound 7b or a mixture of compound 7b and 7c affords the compound of formula I. The oxidation step may be achieved using at least one oxidizing agent such as peroxohydrates. Peroxohydrates are crystalline adducts containing molecular hydrogen peroxide, for example, sodium carbonate peroxohydrate (known commercially as sodium percarbonate, e.g., $Na_2CO_3 \cdot 1.5\ H_2O_2$), urea peroxohydrate ($CO(NH_2)_2 \cdot H_2O_2$), the peroxohydrate of melamine, ($C_3H_6N_6 \cdot H_2O_2$), sodium pyrophosphate peroxohydrate ($Na_4P_2O_7 \cdot 2\ H_2O_2$), sodium sulfate peroxohydrate hydrate ($2Na_2SO_4 \cdot H_2O_2 \cdot 2\ H_2O$), potassium carbonate peroxohydrates, rubidium carbonate peroxohydrates, and cesium carbonate peroxohydrates (the last three have the general formula $M_2CO_3 \cdot 3H_2O_2$). The preferred peroxohydrate for this oxidization step is sodium carbonate peroxohydrate.

Scheme 8
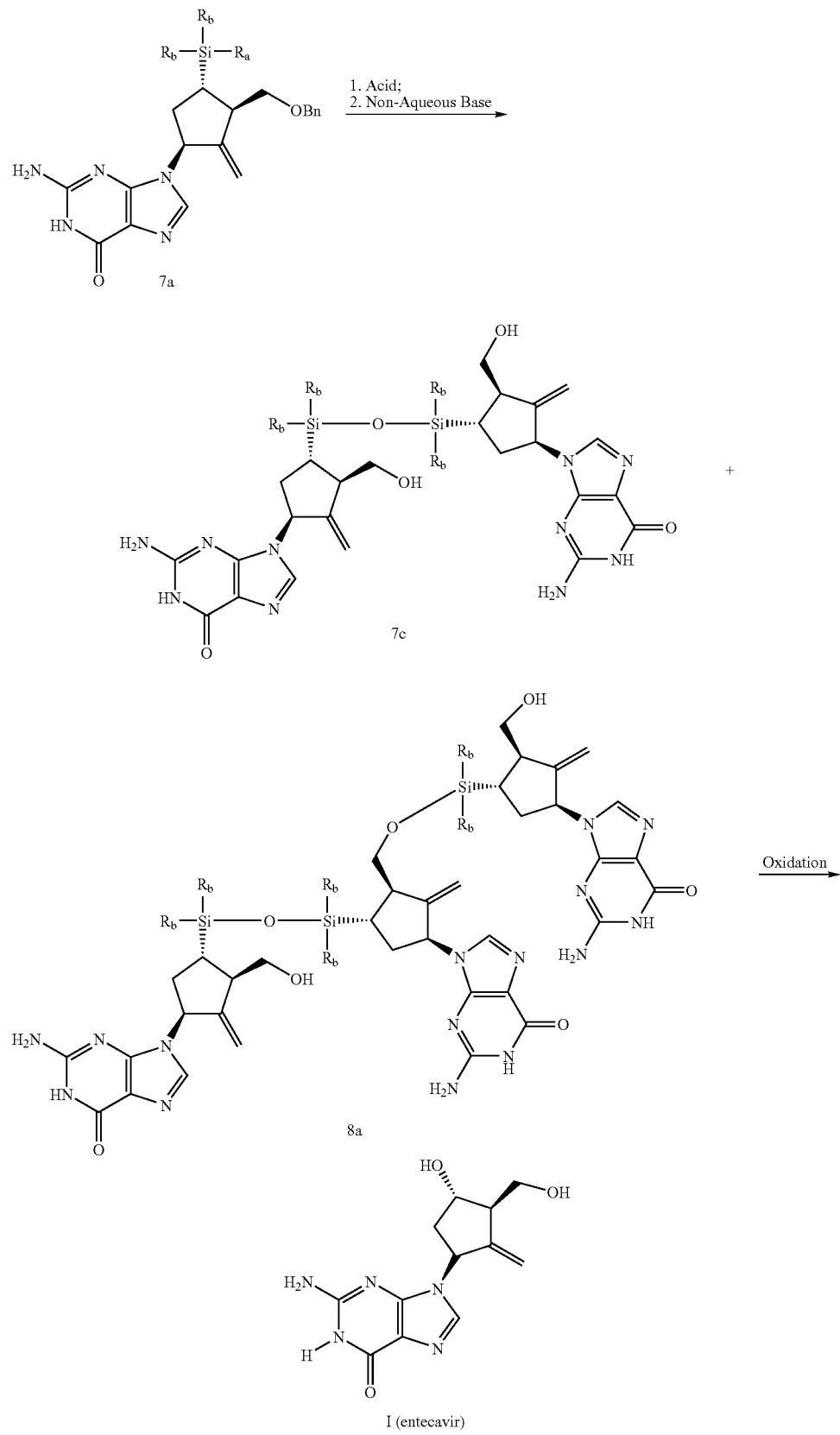

Alternatively, compound 7a can be treated with at least one acid selected from: (i) halogenated methanesulfonic acids; and (ii) optionally methanesulfonic acid as discussed above, followed by treatment with at least one non-aqueous base (e.g., $NR^eR^fR^g$, wherein $R^e$, $R^f$ and $R^g$ are independently hydrogen, alkyl, cycloalkyl, aryl, or said $R^g$ and $R^f$ together with the N to which they are bonded optionally form a heterocycle), to give the compound of formula 7c as the major product (typically about 80% to about 95% yield). Illustrative bases include tertiary amine bases such as triethylamine, N,N-dimethylethylamine, diisopropylethylamine (Hunig's base) or tetramethylenediamine (TMEDA), or a nitrogen containing heterocycle, such as pyridine. The compound of formula 8a may also be formed with up to 20% yield (for example, 5%, 10% or 15%). Further, oxidation of compound 7c or a mixture of compound 7c and 8a affords the compound of formula I. The oxidation step may be achieved using at least one oxidizing agent such as peroxohydrates (e.g., sodium carbonate peroxohydrate) as discussed above.

The following examples further illustrate the present invention, but should not be construed in any way to limit its scope.

EXAMPLE 1

Preparation of Compound 1b'

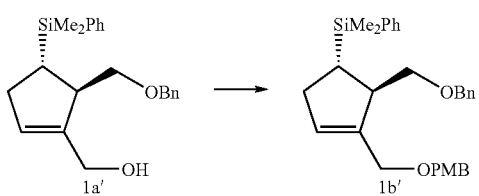

Compound 1a' (6.02 g, 17.1 mmol, 1.00 equiv) was dissolved in toluene (6.70 mL). PMB-Cl (para-methoxybenzyl chloride) (7.00 mL, 51.2 mmol, 3.00 equiv) was added followed by TBAHS (tetrabutylammonium hydrogen sulfate) (0.577 g, 1.71 mmol, 0.0100 equiv) and 50% NaOH (6.70 mL). The reaction was stirred for four hours at room temperature. The reaction mixture was combined with water (23 mL) and toluene (50 mL) and the phases were split. The organic layer was washed again with water (23 mL) and the phases were split. The combined aqueous layers were extracted with toluene (50 mL) and the combined organic layers were concentrated by rotary evaporation. Column chromatography of the crude material was done using a 120 gram silica column and a mobile phase gradient of 2-15% ethyl acetate in hexanes. The desired fractions were combined and concentrated to give the compound of formula 1b' (6.17 g) as yellow oil in 76% yield. $^1$H NMR (360 MHz, $CDCl_3$) δ 7.54-7.52 (m, 2H) 7.35-7.22 (m, 9H), 6.92-6.87 (m, 3H), 5.71 (s, 1H), 4.49-4.35 (m, 4H), 4.06-4.04 (m, 2H), 3.84 (s, 3H), 3.41-3.37 (m, 1H), 3.30-3.28 (m, 1H), 2.92 (s, 1H), 2.57-2.56 (m, 1H), 2.33-2.31 (m, 1H), 1.64-1.59 (m, 1H), 0.27 (s, 6H); $^{13}$C NMR (90 MHz, $CDCl_3$) δ 159.5, 142.8, 139.0, 138.9, 134.3, 131.0, 129.8, 129.7, 129.3, 129.0, 128.7, 128.7, 128.2, 128.1, 114.2, 114.1, 77.6, 73.4, 72.1, 68.1, 55.7, 48.4, 33.8, 25.6, -4.2, -4.2; MS (infusion)=473 ($M+H^+$); HRMS m/e calc'd for $C_{30}H_{37}O_3Si$ ($M+H^+$): 473.2512, found 473.2501.

EXAMPLE 2

Preparation of Compound 1c'

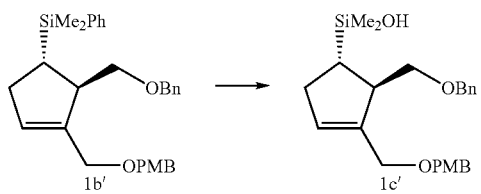

Compound 1b' (6.17 g, 13.1 mmol, 1.00 equiv) was dissolved in DMSO (62 mL) and potassium t-butoxide (5.00 g, 44.0 mmol, 3.37 equiv) was added forming thick slurry. The reaction was stirred at room temperature overnight after which the starting material was not detected by HPLC. The reaction mixture was transferred to a separatory funnel and ethyl acetate (124 mL) and water (124 mL) were charged. The phases were split and the aqueous layer was extracted twice with ethyl acetate (2×124 mL). The combined organic layer was concentrated to a residue and purified by column chromatography using a 120 gram silica column and a mobile phase gradient of 10-50% ethyl acetate in hexanes. The desired fractions were combined and concentrated to give the compound of formula 1c' (3.50 g) as yellow oil in 65% yield. $^1$H NMR (360 MHz, $CDCl_3$) δ 7.25-7.15 (m, 5H) 7.10 (d, J=8.6 Hz, 2H), 6.75 (d, J=8.6 Hz, 2H), 5.63 (s, 1H), 4.40 (q, J=11.9 Hz, 2H), 4.26 (q, J=11.3 Hz, 2H), 3.85 (s, 2H), 3.72-3.70 (m, 1H), 3.68 (s, 3H), 3.42 (bs, 1H), 3.15-3.10 (m, 1H), 2.93 (s, 1H), 2.36-2.33 (m, 1H), 2.09-2.05 (m, 1H), 1.21 (q, J=9.3 Hz, 1H), 0.00 (s, 3H), -0.05 (s, 3H); $^{13}$C NMR (90 MHz, $CDCl_3$) δ 160.4, 142.0, 138.7, 131.9, 131.5, 130.6, 129.7, 129.2, 129.1, 114.9, 76.1, 74.8, 73.0, 68.5, 56.5, 49.5, 34.3, 32.2, 0.0, -1.6; MS (infusion)=413 ($M+H^+$); HRMS m/e calc'd for $C_{24}H_{33}O_4Si$ ($M+H^+$): 413.2148, found 413.2163.

EXAMPLE 3

Preparation of Compound 1d

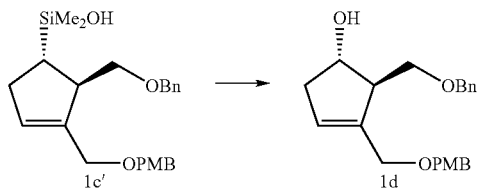

The compound of formula 1c' (1.00 g, 2.42 mmol, 1.00 equiv) was dissolved in methanol (25 mL) and was heated to 65° C. $KHCO_3$ (0.726 g, 7.26 mmol, 3.00 equiv) was dissolved in water (3.4 mL) and added to the reaction. KF (0.281 g, 4.84 mmol, 2.00 equiv) was dissolved in water (0.8 mL) and added to the reaction. A 30% weight solution of $H_2O_2$ (0.840 mL, 7.26 mmol, 3.00 equiv) was added portion-wise over 30 minutes. The reaction was stirred at 68OC for 4.5 hours at which point the starting material was not detected by HPLC. The reaction was cooled to 10° C. NaHSO$_3$ (1.10 g) was dissolved in water (2 mL) and added to the reaction mixture which was warmed to room temperature and stirred until peroxide was no longer evident by peroxide strip testing. The mixture was passed through a Celite pad which was washed with ethyl acetate (2×25 mL). The organic layer was washed with water (20 mL) and 10% brine (10 mL). The organic layer was dried over Na$_2$SO$_4$ and concentrated. The compound of formula 1d as crude yellow oil (0.860 grams, quantitative yield) was carried forward to the next reaction without further purification. $^1$H NMR (360 MHz, CDCl$_3$) δ 7.29-7.20 (m, 5H) 7.15 (d, J=8.7 Hz, 2H), 6.79 (d, J=8.9 Hz, 2H), 5.59 (s, 1H), 4.41 (q, J=12.1 Hz, 2H), 4.32 (q, J=11.4 Hz, 2H), 3.89 (s, 2H), 3.73 (s, 3H), 3.63 (dd, J=9.1, 4.6 Hz, 1H), 3.30 (t, J=8.8 Hz, 1H), 2.79-2.77 (m, 1H), 2.69 (dd, J=22.8, 10.8 Hz, 1H), 2.22 (dd, J=19.2, 4.3 Hz, 1H), 2.05 (bs, 1H); $^{13}$C NMR (90 MHz, CDCl$_3$) δ 159.6, 139.5, 138.9, 130.7, 129.8, 128.8, 128.1, 128.0, 127.5, 114.2, 77.6, 73.7, 72.2, 71.5, 67.9, 55.7, 55.2, 40.2; MS (infusion)=355 (M+H$^+$); HRMS m/e calc'd for C$_{22}$H$_{27}$O$_4$(M+H$^+$): 355.1909, found 355.1917.

EXAMPLE 4

Preparation of Compound 1e

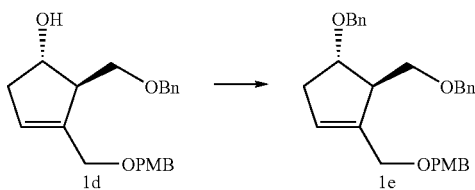

The compound of formula 1d (0.880 g, 2.50 mmol, 1.00 equiv) was dissolved in toluene (4.4 mL) and cooled to 6° C. A solution of KHMDS (potassium bis(trimethylsilyl)amide) in toluene (0.75 M, 6.70 mL, 5.00 mmol, 2.00 equiv) was added drop wise followed by benzyl bromide (0.330 mL, 2.75 mmol, 1.10 equiv). The reaction was warmed to room temperature. The reaction was then cooled to 10° C. and KHMDS (2.00 mL) was charged three times (every two hours) as the reaction appeared to stall. The reaction was stirred overnight, cooled to 10° C., and additional toluene (4.4 mL), KHMDS (2.00 mL), and BnBr (0.0300 mL) were charged. The reaction was stirred an additional 42 hours after which time 3.6 RAP compound Ed remained. The reaction was quenched with 1 M HCl until the apparent pH was 7. The reaction mixture was transferred to a separatory funnel with toluene (20 mL) and water (10 mL). The phases were split and the aqueous was back-extracted with toluene (20 mL). The combined organic was concentrated to a residue. Column chromatography of the crude material was done using a 120 gram silica column and a mobile phase gradient of 1-75% ethyl acetate in hexanes. The desired fractions were combined and concentrated to give the compound of formula 1e (0.600 g) as a yellow oil in 55% yield for two steps. $^1$H NMR (360 MHz, CDCl$_3$) δ 7.24-7.15 (m, 10H) 7.13 (d, J=8.7 Hz, 2H), 6.75 (d, J=8.6 Hz, 2H), 5.60 (s, 1H), 4.43 (s, 2H), 4.37 (q, J=6.7 Hz, 2H), 4.33-4.24 (m, 2H), 4.12-4.09 (m, 1H), 3.93 (s, 2H), 3.69 (s, 3H), 3.48 (dd, J=9.5, 4.5 Hz, 1H), 3.30 (dd, J=9.5, 6.7 Hz, 1H), 2.93 (s, 1H), 2.60 (dd, J=17.2, 10.6 Hz, 1H), 2.30 (d, J=17.0, 1H); $^{13}$C NMR (90 MHz, CDCl$_3$) δ 159.5, 140.0, 139.2, 138.9, 130.9, 129.8, 128.7, 128.1, 128.0, 127.9, 127.8, 127.5, 114.1, 82.4, 73.5, 72.0, 71.1, 70.2, 68.0, 55.7, 53.2, 38.5; MS (infusion)=445 (M+H$^+$); HRMS m/e calc'd for C$_{29}$H$_{33}$O$_4$(M+H$^+$): 445.2379, found 445.2389.

EXAMPLE 5

Preparation of Compound 1f

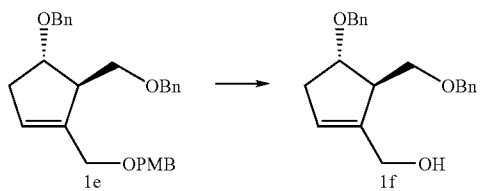

The compound of formula 1e (0.500 g, 1.13 mmol, 1.00 equiv) was dissolved in CH$_2$Cl$_2$ (11.7 mL) and water (0.93 mL) was added. The reaction mixture was cooled to 2° C. and DDQ (2,3-dichloro-5,6-dicyano-1,4-benzoquinone) (0.383 g, 1.69 mmol, 1.50 equiv) was added. The solution turned black. The mixture was stirred at 0-2° C. for two hours at which time 1.3 RAP of the starting material remained by HPLC. 5% aqueous NaHCO$_3$ (10 mL) was added followed by water (10 mL). The phases were split. The aqueous layer was extracted three times with CH$_2$Cl$_2$ (3×25 mL). The combined organic phase was washed with water (20 mL) and concentrated to a residue. Column chromatography of the crude material was done using a 120 gram silica column and a mobile phase gradient of 10-100% ethyl acetate in hexanes. The desired fractions were combined and concentrated to give the compound of formula 1f (0.250 g) as a yellow oil in 69% yield. $^1$H NMR (360 MHz, CDCl$_3$) δ 7.37-7.25 (m, 10H) 5.62 (s, 1H), 4.53 (s, 2H), 4.22 (q, J=11.8 Hz, 2H), 4.14 (s, 2H), 4.02-3.97 (m, 1H), 3.61 (dd, J=9.0, 5.0 Hz, 1H), 3.46 (dd, J=16.8, 8.4 Hz, 1H), 3.06 (s, 1H), 2.64 (dd, J=16.8, 7.0 Hz, 1H), 2.45 (bs, 1H); 2.37 (dd, J=17.1, 1.9 Hz, 1H); $^{13}$C NMR (90 MHz, CDCl$_3$) δ 143.6, 138.8, 137.9, 128.9, 128.8, 128.3, 128.3, 128.1, 128.0, 126.1, 82.3, 73.9, 71.6, 71.4, 61.5, 52.9, 38.0; MS (infusion)=325 (M+H$^+$); HRMS m/e calc'd for C$_{21}$H$_{25}$O$_3$(M+H$^+$): 325.1804, found 325.1808.

EXAMPLE 6

Preparation of Compound 2a'

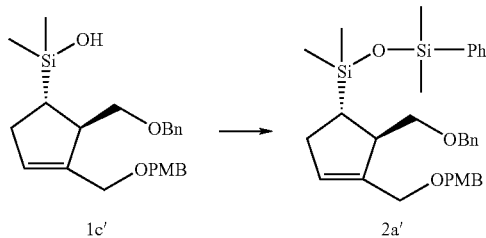

The compound of formula 1c' (2.00 g, 4.80 mmol, 1.00 equiv) was dissolved in DMF (74 mL) and imidazole (1.97 g, 29.0 mmol, 6.00 equiv) was added. The mixture was cooled to 0-5° C. followed by drop wise addition of Ph(CH$_3$)$_2$SiCl (3.40 mL, 20.2 mmol, 4.20 equiv) while maintaining temperature 0-5° C. The reaction mixture was stirred at 25° C. for 42 hours. The reaction mixture was diluted with water (50 mL) and diethyl ether (50 mL). Phases were separated and the aqueous phase was back-extracted with diethyl ether (50 mL). The combined organic phase was concentrated on a rotavap to a light yellow oil and purified by column chromatography (0-75% EtOAc in hexanes) to give 1.95 grams (74% yield) of compound 2a' as a light yellow oil (AP=93.7%). $^1$H NMR (360 MHz, CD$_2$Cl$_2$) δ 7.19 (d, 2H), 6.98-6.91 (m, 8H), 6.86 (d, 2H), 6.52 (d, 2H), 5.32 (s, 1H), 4.04 (s, 2H), 4.02 (q, 2H), 3.67 (q, 2H), 3.42 (s, 3H), 3.08-3.03 (m, 2H), 2.99 (s, 1H), 2.57 (s, 1H), 2.14-2.12 (m, 1H), 1.90-1.87 (m, 1H); 0.99-0.96 (m, 2H), −0.04 (s, 6H), −0.29 (s, 6H); $^{13}$C NMR (90 MHz, CD$_2$Cl$_2$) δ 165.5, 148.5, 145.7, 144.6, 138.8, 135.3, 135.2, 134.8, 134.2, 133.6, 133.2, 119.5, 79.2, 78.8, 77.6, 73.4, 60.5, 38.2, 37.5, 33.5, 28.5, 19.3, 5.9, 3.9.

EXAMPLE 7

Preparation of Compound 2b'

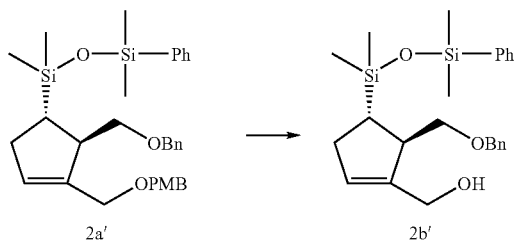

The compound of formula 2a' (4.8 g) was dissolved in CH$_2$Cl$_2$ (110 mL) and water (8.9 mL) and the solution was cooled to 0-5° C. DDQ (30.3 g, 1.50 equiv) was added in one portion. The reaction mixture turned into a blue solution. The reaction was stirred at 0-5° C. until deemed to be complete by HPLC, typically 2 hours. The reaction mixture, a yellow suspension, was diluted with 5% aqueous NaHCO$_3$ (80 mL) and water (90 mL). The phases were separated. The aqueous phase was extracted with CH$_2$Cl$_2$ (2×50 mL). The combined organic phase was washed with water (50 mL) and evaporated to a residue which was applied to a silica gel column (150 g) that was eluted with 10% EtOAc in hexanes to give the compound of formula 2b' as a colorless oil (2.6 g, 69% yield, 96.8% AP).

EXAMPLE 8

Preparation of Compound 2c'

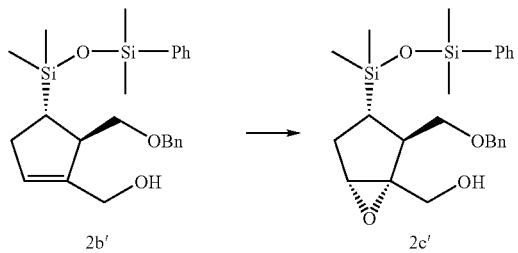

To a dry vessel, 4A° Molecular Sieves (13.0 g) and toluene (13 mL) were charged, the slurry was cooled to −35 to −40° C. under N$_2$. A solution of (−)-DIPT (0.40 g, 0.28 equiv) in toluene (2 mL) was added at −35 to −40° C. The slurry was stirred at −35 to −45° C. for 30 minutes. Titanium (IV) isoproxide (0.43 mL, 0.24 equiv) was added to the tartrate solution and stirred at −35 to −45° C. for 30 min. Then a solution of compound 2b' (2.6 g, 1.0 equiv) in 13 mL of toluene was added over 5 minutes while maintaining the temperature at −35 to −40° C. The resulting brown slurry was stirred at −35 to −40° C. for 1-1.5 h. tert-Butyl hydroperoxide (5.5M in decane, 2.2 mL, 2.0 equiv) was added to reaction mixture over 10 min. at −35 to −45° C. The reaction was stirred at −35 to −45° C. until the epoxidation was deemed complete by HPLC, typically 3-5 h. Upon completion of the reaction, 30% NaOH saturated with sodium chloride (0.9 mL) was added to quench the titanium-tartrate catalyst and to hydrolyze (−)-DEPT. A solution of sodium bisulfite (1.4 g) in water (3.2 mL) was added over 10 min while maintaining the temperature between 10-30° C. This was stirred for 1-3 h until a peroxide test strip tested negative for peroxides. Celite (3.2 g) was charged, and the reaction mixture was filtered. The filter cake was washed with toluene (2×20 mL). The filtrate was washed with 5% NaHCO$_3$ (20 mL), and 10% NaCl (20 mL). The resulting solution is evaporated to give the compound of formula 2c' as a yellow oil (2.1 g, 78% yield, 89% AP). $^1$H NMR (360 MHz, CD$_2$Cl$_2$) δ 7.25-7.21 (m, 2H), 7.04-6.98 (m, 8H), 5.32 (s, 1H), 4.13 (s, 2H), 3.83 (q, 2H), 3.18-3.04 (m, 2H), 2.59 (s, 1H), 2.20-2.16 (m, 1H), 1.95-1.91 (m, 1H); 0.95-0.92 (m, 2H), −0.01 (s, 6H), −0.25 (s, 6H); $^{13}$C NMR (90 MHz, CD$_2$Cl$_2$) δ 151.8, 145.7, 144.4, 138.8, 135.2, 134.2, 133.7, 133.5, 132.2, 79.8, 78.9, 66.2, 53.8, 38.1, 37.5, 33.7, 28.5, 19.3, 5.8, 3.8.

EXAMPLE 9

Preparation of Compound 2d'

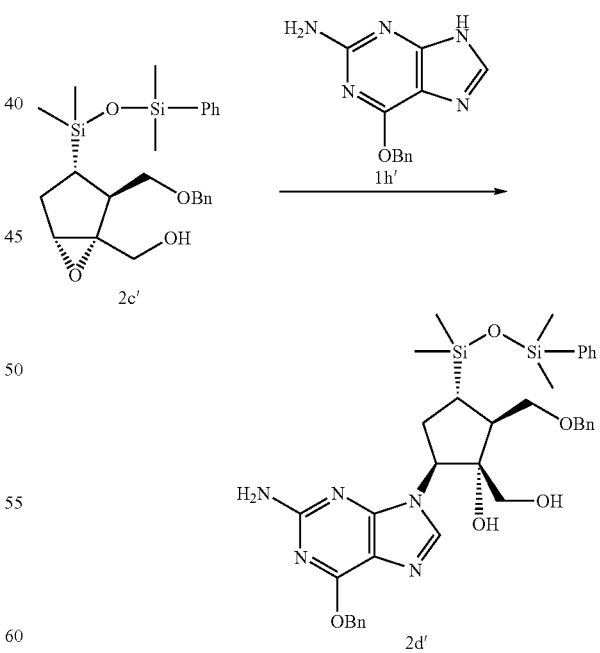

To a mixture of compound 2c' (2.1 g) and compound 1h' (1.30 g, 1.15 equiv) in DMF (10 mL), LiOH (0.10 g, 0.87 equiv) was charged. The resulting solution was heated at 90° C. until deemed to be complete by HPLC, typically 4 h. The reaction was cooled to room temperature and was diluted with EtOAc (30 mL) and water (30 mL). The pH was adjusted from 12.0 to 5.1 by addition of 1M HCl (2.4 mL). The reaction mixture was then extracted with EtOAc (2×35 mL). The combined organic phase was washed with brine (2×30 mL) and evaporated to a residue. The crude oil was purified using column chromatography and was eluted with 20 to 50% EtOAc in hexanes to give the compound of formula 2d' as a white solid (0.74 g, 23.8% yield, 96.9% AP). $^1$H NMR (360 MHz, CDCl$_3$) δ 7.55-7.50 (m, 4H), 7.36-7.22 (m, 11H), 5.57 (q, 2H), 4.90 (s, 2H), 4.41 (s 2H), 4.40-4.36 (m, 1H), 3.55 (dd, 2H), 3.38 (dd, 2H), 2.70 (q, 1H), 2.38-2.36 (m, 1H), 2.14-2.10 (m, 1H), 1.52-1.48 (m, 1H), 0.36 (s, 3H), 0.35 (s, 1H), 0.12 (s, 3H), 0.11 (s, 3H); $^{13}$C NMR (90 MHz, CDCl$_3$) δ 161.4, 158.1, 154.0, 139.5, 137.3, 136.2, 132.9, 129.5, 128.5, 128.3, 127.9, 127.8, 116.0, 82.3, 73.5, 69.3, 68.3, 65.1, 62.7, 48.4, 27.1, 23.7, 0.7, 0.6, −1.2, −1.2; HRMS m/e calc'd for C$_{36}$H$_{45}$N$_5$O$_5$Si$_2$ (M+H$^+$): 684.3038, found 684.3031.

EXAMPLE 10

Preparation of Compound 2e'

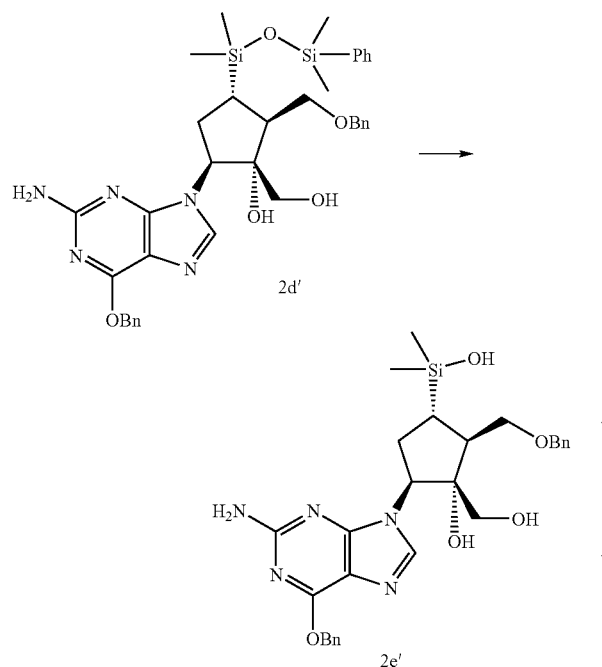

Condition (1): the compound of formula 2d' (20 mg, 0.029 mmol, 1.0 equiv) was dissolved in THF (0.200 mL) and was cooled to 0° C. Tetrabutylammonium fluoride (TBAF) (0.030 mL, 0.029 mmol, 1.0 M in THF, 1.0 equiv) was added and the reaction was warmed to room temperature. The reaction appeared to stall after two hours, the reaction was then cooled to 0° C. and additional TBAF (0.030 mL, 0.029 mmol, 1.0 M in THF, 1.0 equiv) was added. This was repeated three times until a 95% conversion was achieved. The material was transferred to a pipet column and eluted using a gradient of 25% ethyl acetate in hexanes to 100% ethyl acetate, and 10-30% methanol in ethyl acetate. The product of formula 2e' was contaminated with its dimer.

Condition (2): the reaction was repeated using CSA in CH$_2$Cl$_2$ and CH$_3$OH, and the product of formula 2e' contained 3% of its dimer.

Condition (3): the reaction was repeated using basic conditions with 10 N NaOH in THF, and the product 2e' contained only 0.65% dimer, but the reaction stalled at 91% conversion. After purification, the product was isolated in 71 AP.

Condition (4): the reaction was repeated using potassium t-butoxide (22 mg, 0.18 mmol, 8.0 equiv) and DMSO (0.15 mL) and after one hour no starting material was evident. Water (0.4 mL) was added along with ~1 mg seed and the reaction mixture was cooled to 0° C. and stirred 30 minutes. The slurry was filtered and washed with water (2 mL) and dried at 40° C. to give the compound of formula 2e' as an orange solid in 58% yield.

EXAMPLE 11

Alternative Preparation of Compound 2e'

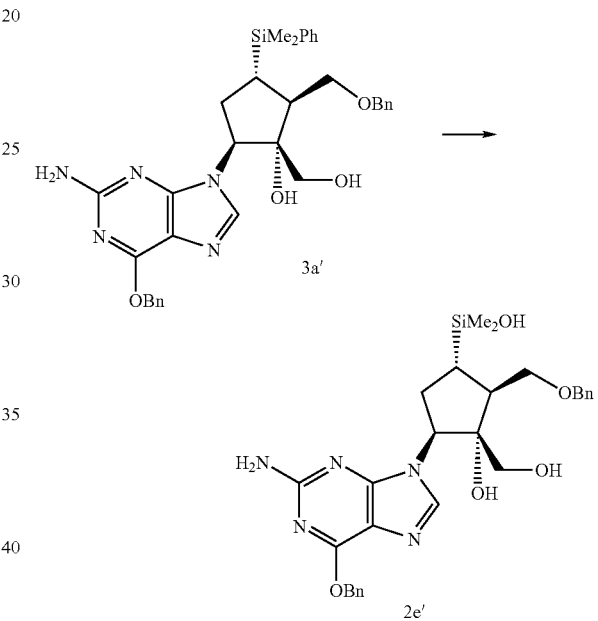

The compound of formula 3a' (disclosed in PCT patent application PCT/US03/39554 and U.S. patent application Ser. No. 10/734,012, as the compound of formula 78A) (10.0 g, 16.4 mmol, 1.00 equiv) was dissolved in DMSO (100 mL) to give a light brown solution which was cooled to 13° C. using an ice bath. Potassium tert-butoxide (14.4 g, 131 mmol, 8.00 equiv) was added to give thick light brown slurry which was warmed to room temperature. After two hours 0.1 RAP of the starting material remained by HPLC. The reaction mixture was added portion wise to water (600 mL) at 13-15° C. The pH was adjusted to 8.2 with 6 M HCl and the slurry was filtered and washed with water (2×100 mL). The material was dried at 40° C. for 60 hours. Several small scale purifications were attempted. The best results were obtained by slurrying the light brown solid (3.90 g) in ethyl acetate (20 mL), filtering and washing the cake with ethyl acetate (2×20 mL). After combining the different batches, the compound of formula 2e' (6.48 g total) was isolated as an off-white solid with impurity profiles ranging from 91.6-96.0 AP (72% yield). $^1$H NMR (360 MHz, CDCl$_3$) δ 7.50 (s, 1H), 7.32 (d, J=8.2 Hz, 2H), 7.21-7.07 (m, 8H), 5.39 (q, 2H), 4.93 (s, 1H), 4.39 (m, 1H), 4.28 (q, 2H), 3.41 (dd, J=9.3, 5.7 Hz, 1H), 3.33-3.31 (m, 1H), 3.18 (q, 2H), 2.43-2.40 (m, 1H), 2.33-2.28 (m, 1H); 2.17-2.11

(m, 1H) 1.37-1.31 (m, 1H), 0.00 (s, 3H), 0.00 (s, 3H); $^{13}$C NMR (90 MHz, CDCl$_3$) δ 162.9, 159.0, 139.8, 138.4, 137.1, 129.8, 129.7, 129.7, 129.5, 129.3, 129.3, 116.9, 84.1, 74.9, 71.5, 69.9, 65.5, 63.1, 49.9, 28.9, 27.0, −0.0, −1.2; HRMS m/e calc'd for C$_{28}$H$_{36}$N$_5$O$_5$Si (M+H$^+$): 550.2486, found 550.2477; mp=163.2.

EXAMPLE 12

Preparation of Compound 3f'

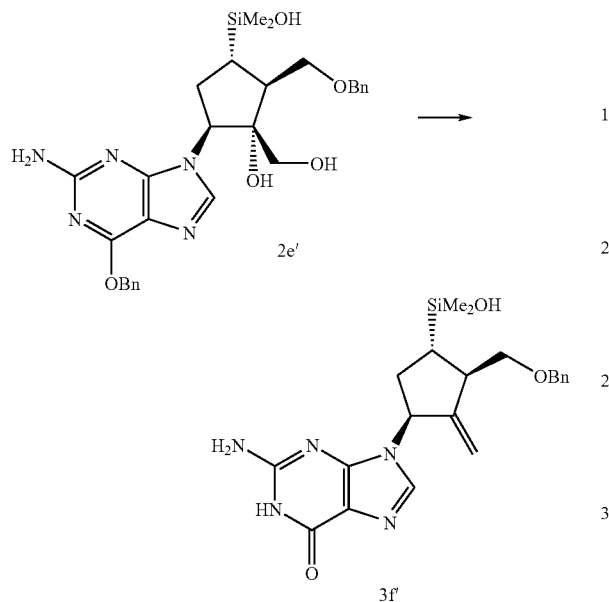

The compound of formula 2' (1.00 g, 1.80 mmol, 1.00 equiv) was slurried in toluene (6 mL). TFA (trifluoroacetic acid) (0.110 mL, 1.40 mmol, 0.750 equiv) was added followed by TIOF (triisopropylorthoformate) (1.22 mL, 5.40 mmol, 3.00 equiv). The resulting brown solution was stirred at room temperature for one hour at which point 0.54 AP of compound 2e' was remaining by HPLC. BHT (2,6-Di-tert-butyl-4-methylphenol) (1.00 g) was added followed by acetic anhydride (2.00 mL) and acetic acid (0.210 mL, 3.60 mmol, 2.00 equiv). The reaction mixture was warmed to 116° C. and the distillate (4 mL) was collected. Toluene (2 mL) was charged and the reaction was continued for 14 hours and cooled to room temperature. Methanol (6.0 mL) was charged to a separate round bottom flask and was cooled to 14° C. 6 M HCl (2.7 mL) was added to the methanol. The reaction mixture was added drop wise followed by a methanol rinse (2.0 mL) of the reaction flask. The reaction mixture was warmed to 25° C. and then heated to 68° C. After five hours no change was detected by HPLC. The reaction was cooled to 25° C. and transferred to a separatory funnel using methanol (2 mL). The reaction mixture was washed a total of six times with heptane (4×6 mL, 2×10 mL) which lowered the BHT to 0.33 AP. After two extractions of the mixture with ethyl acetate (2×20 mL) the combined organic phase was dried over Na$_2$SO$_4$ and concentrated. Column chromatography of the crude material was done on a 120 gram silica column and a mobile phase gradient of 40-100% ethyl acetate in hexanes followed by 10% methanol in ethyl acetate. The desired fractions were combined and concentrated to give the compound of formula 3f' (0.160 g, 20% yield) but an impurity identified as the dimer of compound 3f' by LC-MS was present. The material was re-slurried in 25:75 hexane:ethyl acetate and filtered to give a white solid with only trace dimer present by HPLC. $^1$H NMR (360 MHz, CD$_3$OD) δ 7.80 (s, 1H), 7.34-7.27 (m, 5H), 5.31-5.27

(m, 1H), 5.30 (s, 1H), 5.02 (s, 1H), 4.57 (s, 2H), 3.78 (dd, J=9.3, 4.8 Hz, 2H), 3.71 (dd, J=9.3, 4.8 Hz, 1H), 2.84 (s, 1H), 2.17-2.13 (m, 2H); 1.39-1.37 (m, 1H), −0.00 (s, 6H); $^{13}$C NMR (90 MHz, CD$_3$OD) δ 159.4, 155.2, 153.9, 153.1, 139.6, 138.6, 129.5, 129.0, 128.8, 117.4, 112.1, 74.3, 73.6, 59.7, 45.8, 34.9, 28.3, −1.31; MS (LC-MS)=426 (M+H$^+$); HRMS m/e calc'd for C$_{21}$H$_{28}$N$_5$O$_3$Si (M+H$^+$): 426.1961, found 426.1963; mp=193.3° C.

EXAMPLE 13

Preparation of Compound 5a'

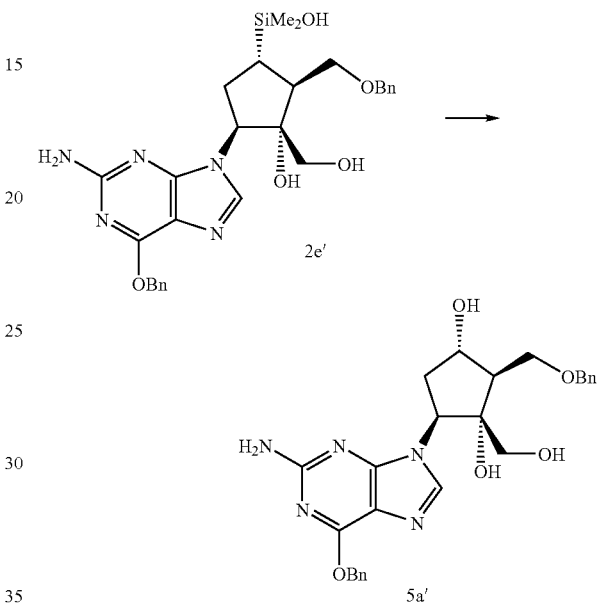

The compound of formula 2e' (2.00 g, 3.64 mmol, 1.00 equiv) was dissolved in methanol (50 mL) and warmed to 65° C. KHCO$_3$ (1.09 g, 10.9 mmol, 3.00 equiv) was dissolved in water (5.0 mL) and added to the reaction. KF (0.423 g, 7.28 mmol, 2.00 equiv) was dissolved in water (1.2 mL) and added to the reaction. A 30% weight solution of H$_2$O$_2$ (1.20 mL, 10.9 mmol, 3.00 equiv) was added portion wise over 30 minutes. The reaction was stirred at 68° C. for 3 hours at which point additional H$_2$O$_2$ (1.20 mL, 10.9 mmol, 3.00 equiv) was added. After 4 hours H$_2$O$_2$ (0.600 mL, 5.45 mmol, 1.50 equiv) was added. The reaction was cooled to 25° C. and the pH was adjusted to 7 with 6M HCl. NaHSO$_3$ (2.80 g) was dissolved in water (6 mL) and added to the reaction mixture at 10° C. which was then warmed to room temperature and stirred until peroxide was no longer evident by peroxide strip testing. The mixture was concentrated to remove methanol. Water (20 mL) and ethyl acetate (100 mL) were charged and the phases were split. The aqueous layer was extracted twice with ethyl acetate (2×100 mL) and the combined organic was concentrated. The resulting solid was slurried in ethyl acetate (20 mL) and filtered. The cake was washed with ethyl acetate (50 mL) and water (30 mL). The cake was dried at 40° C. giving the compound of formula 5a' as a white solid (1.78 grams, quantitative yield) which was carried forward to the next reaction without further purification. $^1$H NMR (360 MHz, DMSO-d$_6$) δ 7.62 (s, 1H), 7.27 (d, J=7 Hz, 2H), 7.18-7.02 (m, 8H), 6.33 (s, 2H), 5.26 (t, J=12.7 Hz, 2H), 4.87 (s, 1H), 4.77-4.67 (m, 2H), 4.59 (d, J=5.2 Hz, 1H), 4.28 (s, 2H), 3.88 (q, J=5.9 Hz, 1H), 3.59-3.46 (m, 2H), 3.08-3.06 (m, 1H), 2.81 (dd, J=11.5, 4.9 Hz, 1H), 2.64 (q, J=8.9 Hz, 1H), 2.07 (q, J=6.6 Hz, 1H), 1.66 (t, J=11.6 Hz, 1H); $^{13}$C NMR (90 MHz, DMSO-d$_6$) δ 160.5, 159.5, 155.3, 140.1, 139.0, 137.0, 128.9, 128.8, 128.6, 128.4, 127.9, 127.7, 114.1, 81.3, 72.4, 69.9, 68.9, 67.2, 62.5, 61.8, 56.5, 37.5; MS (infusion)=492 (M+H$^+$); HRMS m/e calc'd for C$_{26}$H$_{30}$N$_5$O$_5$ (M+H$^+$): 492.2247, found 492.2262.

EXAMPLE 14

Preparation of Compound 5e

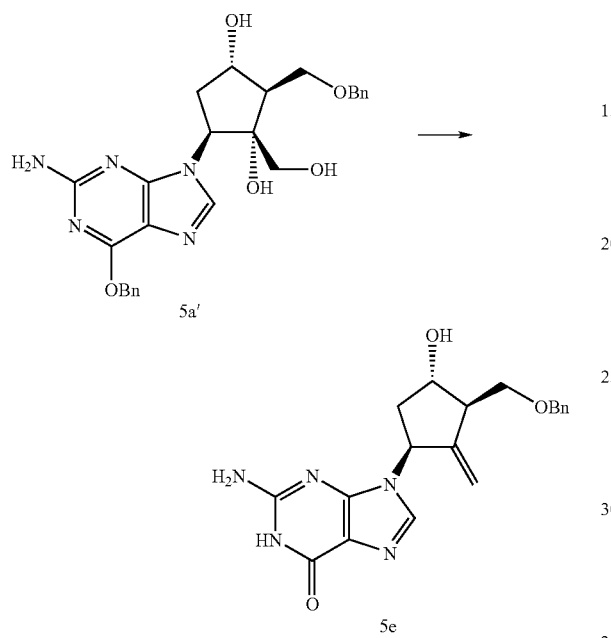

The compound of formula 5a' (1.00 g, 2.04 mmol, 1.00 equiv) was slurried in toluene (6 mL) and CH$_2$Cl$_2$ (2 mL). TFA (trifluoroacetic acid) (0.120 mL, 1.50 mmol, 0.750 equiv) was added followed by TIOF (triisopropylorthoformate) (1.36 mL, 6.12 mmol, 3.00 equiv). The resulting brown solution was stirred at room temperature for one hour at which point 0.22 AP of compound 5a' remained by HPLC. BHT (2,6-Di-tert-butyl-4-methylphenol) (1.00 g) was added followed by acetic anhydride (2.00 mL) and acetic acid (0.230 mL, 3.60 mmol, 2.00 equiv). The reaction mixture was warmed to 116° C. and the distillate (4 mL) was collected. The reaction was continued for 14 hours and cooled to room temperature. Methanol (6.0 mL) was charged to a separate round bottom flask and was cooled to 14° C. 6 M HCl (2.7 mL) was added to the methanol. The reaction mixture was added drop wise followed by a methanol rinse (2.0 mL) of the reaction flask. The reaction mixture was warmed to 25° C. and then heated to 68° C. After five hours the reaction was cooled to 25° C. and transferred to a separatory funnel using methanol (2 mL). The reaction mixture was washed twice with 90% ethyl acetate in heptanes (2×30 mL) and concentrated to a residue. Methanol (9 mL) was added followed by 4 N NaOH to adjust the pH to 8. Brown slurry formed immediately, and it was cooled to 0° C. for 30 minutes and filtered. The cake was washed with water (3×3 mL), and heptane (2×10 mL). Re-slurry of the crude cake in heptanes/ethyl acetate (75:25) did not improve the impurity profile. Solids crashed out of the mother liquor from the previous crystallization and were subjected to column chromatography on silica gel using a gradient of 50-100% ethyl acetate in hexanes followed by 10-30% ethyl acetate in methanol giving 0.210 g of the compound of formula 5e. Column chromatography was repeated on the solids isolated from the re-slurry giving an additional 0.120 g of the compound of formula 5e (44% yield). $^1$H NMR (360 MHz, CD$_3$OD) δ 7.56 (s, 1H), 7.27-7.18 (m, 5H), 5.44-5.39 (m, 1H), 5.14 (s, 1H), 4.70 (s, 1H), 4.48 (q, 2H), 4.30-4.28 (m, 1H) 3.62 (d, J=5.5 Hz, 2H), 2.69 (s, 1H), 2.31-2.24 (m, 1H); 2.14-2.08 (m, 1H); $^{13}$C NMR (90 MHz, CD$_3$OD) δ 159.8, 155.6, 153.8, 152.2, 140.0, 138.8, 129.9, 129.3, 129.2, 117.7, 112.0, 74.7, 73.8, 73.1, 57.4, 53.6, 41.3; MS (infusion)=368 (M+H$^+$); HRMS m/e calc'd for C$_{19}$H$_{23}$N$_5$O$_3$(M+H$^+$): 368.1723, found 368.1722; mp=134.3° C.

EXAMPLE 15

Preparation of Compound I (Entecavir)

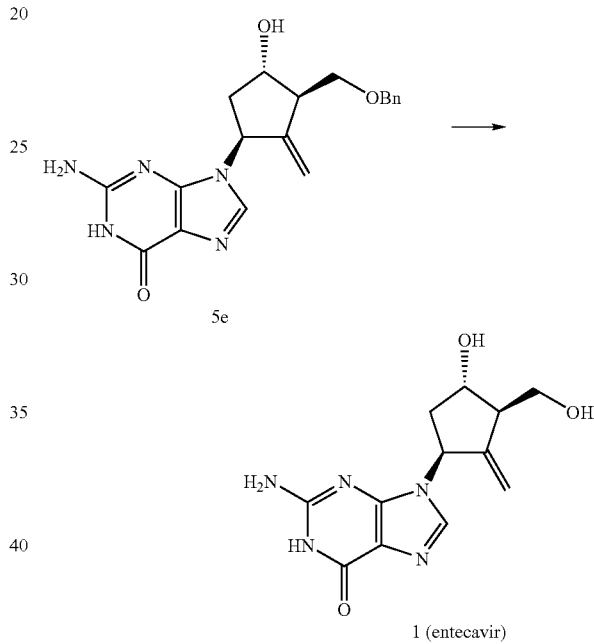

To a solution of 5e (2.0 g, 5.44 mmoles) in methylene chloride (20 mL), cooled to −20° C., was added a methylene chloride solution of boron trichloride (1M, solution, 22 mL. 22 mmoles, 4.04 equivalents) over a period of ~30 minutes. During addition, the temperature was maintained at −19° to −23° C. After stirring for an additional 3 hours at −20° C., methanol (14 mL) was added to quench the reaction. The reaction mixture was stirred until HPLC showed no borane ester (~4 hours). MTBE (30 mL) was added, and the reaction mixture was stirred overnight at room temperature. The solid obtained was filtered, washed with MTBE (~5 mL), and dried under vacuum at room temperature to obtain 1.66 g of the hydrochloride salt of entecavir. The HCl salt (0.72 g, 2.29 mmoles) was taken in ~13 mL of water and heated to ~40° C. The pH was adjusted to ~7 with 2N NaOH. The thin slurry obtained was heated to 80-85° C. and treated with activated carbon (0.12 g). After 30 minutes at reflux, the hot mixture was filtered on a Celite pad. The filtrate was cooled to room temperature over 3 hours and further stirred at 0° C. for 2 hours. The crystals obtained were filtered, washed with water, and dried under vacuum to obtain the compound of formula I (entecavir) (0.32 g, 44% overall yield from 5e).

EXAMPLE 16

Preparation of Compound 7b'

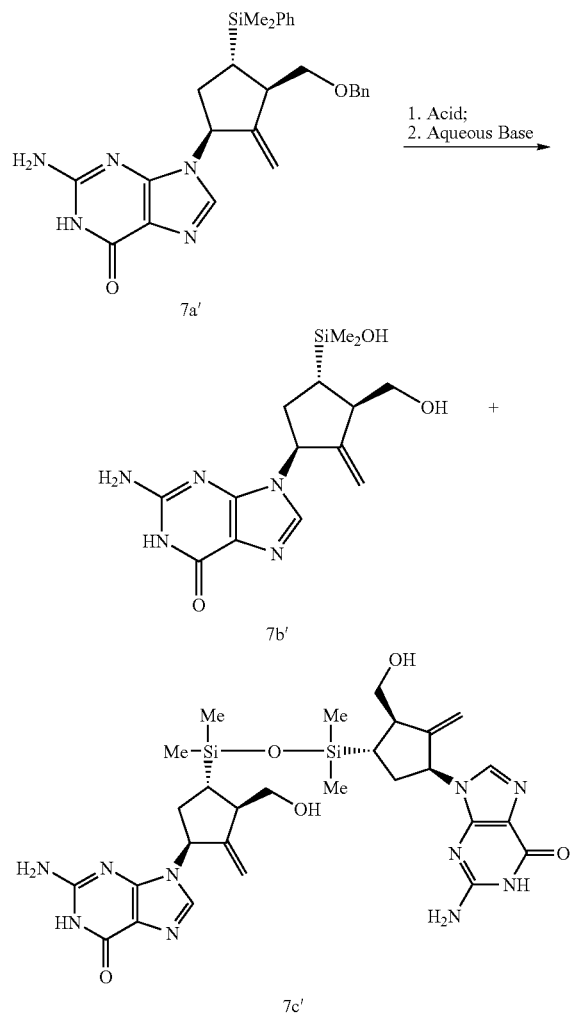

A 1000 mL jacketed vessel equipped with overhead stirrer, thermometer, an addition funnel and a nitrogen inlet was charged with compound 7a' (40 g), DCM (180 mL), and sulfolane (20 mL), and the reaction mixture was cooled to 10 to 15° C. MSA (14.48 g, 2 eq.) was added drop-wise to the vessel while maintaining the temperature of the reaction mixture below 15° C. The reaction mixture was further cooled to between about 5 to 10° C. TFMSA (22 mL, 3.2 eq.) was added slowly to the vessel while maintaining the reaction temperature below about 10° C. The reaction mixture warmed to ambient temperature and stirred overnight. After the reaction was complete as determined by HPLC, the reaction mixture was cooled to 0-10° C., and 2N NaOH (360 mL) was added slowly while maintaining the vessel temperature below 15° C. The resulting slurry was warmed to ambient temperature and allowed to stir for about 1.5 hours. Toluene (600 mL) was added and the mixture stirred for 30 minutes. The rich aqueous solution was washed with toluene (2×600 mL), diluted with water (370-375 mL) and quenched with glacial acetic acid at 80 to 85° C. to bring the pH of the solution to 6.8 to 7.2. After holding the slurry for about 2 h at 80 to 85° C. and at room temperature for 4 h, the slurry was further cooled to 0 to 10° C. and stirred for 1-1.5 h. The slurry was then filtered, washed with water (2×80 mL), heptane (2×80 mL) and dried under vacuum at 55° C. to afford 23.26 g of compound 7b' (84.6% yield) (may contain about 5 to about 15% of compound 7c'). LC/MS for 7c': retention time=5.95 min.; (M+H)=653. (HPLC condition: Solvent A: 5% $CH_3CN$, 95% $H_2O$, 10 mM $NH_4OAc$; Solvent B: 95% CH3CN, 5% $H_2O$, 10 nM $NH_4OAc$; Gradient Time: 15 min.; Start % B=0' Final % B=100; Flow rate 2.2 ml/min.; column =Luna C18, 50×4.6 mm; wavelength=210 nM)

EXAMPLE 17

Preparation of Compound I (Entecavir)

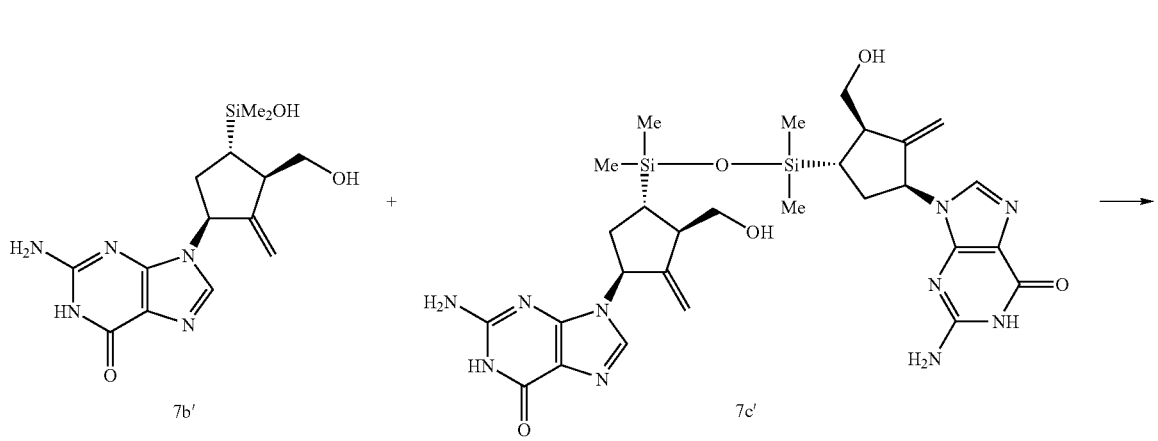

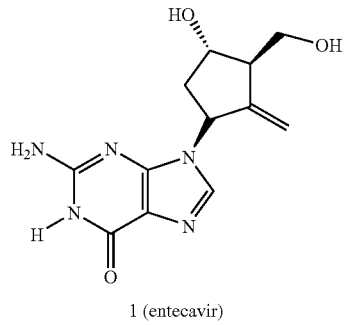

1 (entecavir)

A 500 mL 3-necked round bottom flask equipped with overhead stirrer, a condenser and a thermometer was charged with compound 7b' (10 g) (may contain up to to 15% of compound 7c'), sodium carbonate peroxohydrate (14 g), and methanol (250 mL). The reaction mixture was heated to reflux with agitation until the reaction was complete as determined by HPLC. The reaction mixture was then cooled down to room temperature, filtered through a filter paper to give a filter cake, which was rinsed with methanol (5×50 mL). The filtrate was transferred to a 500 mL equipped with a magnetic stirrer and a thermometer, and aqueous sodium thiosulfate (5×50 mL, 0.4 M) was added with agitation until the residual peroxide was quenched. The resulting cloudy solution was filtered through a filter paper while maintaining the temperature of the solution at about 55° C., and the filter cake was rinsed with warm water (45 mL, at 50° C. to 60° C.). To the resulting clear filtrate was added glacial acid while maintaining the temperature of the solution at 70 to 75° C. until the pH of the solution was 6 to 7. The resulting mixture was heated to 90 to 95° C. for about 30 minutes, and then cooled to room temperature slowly with agitation. The resulting slurry was filter collected and washed with cold water (2×50 mL), and dried under vacuum to give the compound of formula I (typical yield: 79 to 85%). Compound I may be further purified through decolorization upon treating with carbon and recrystallization from methanol, water, or a mixture thereof.

EXAMPLE 18

Preparation of Compound 7c' and 8a'

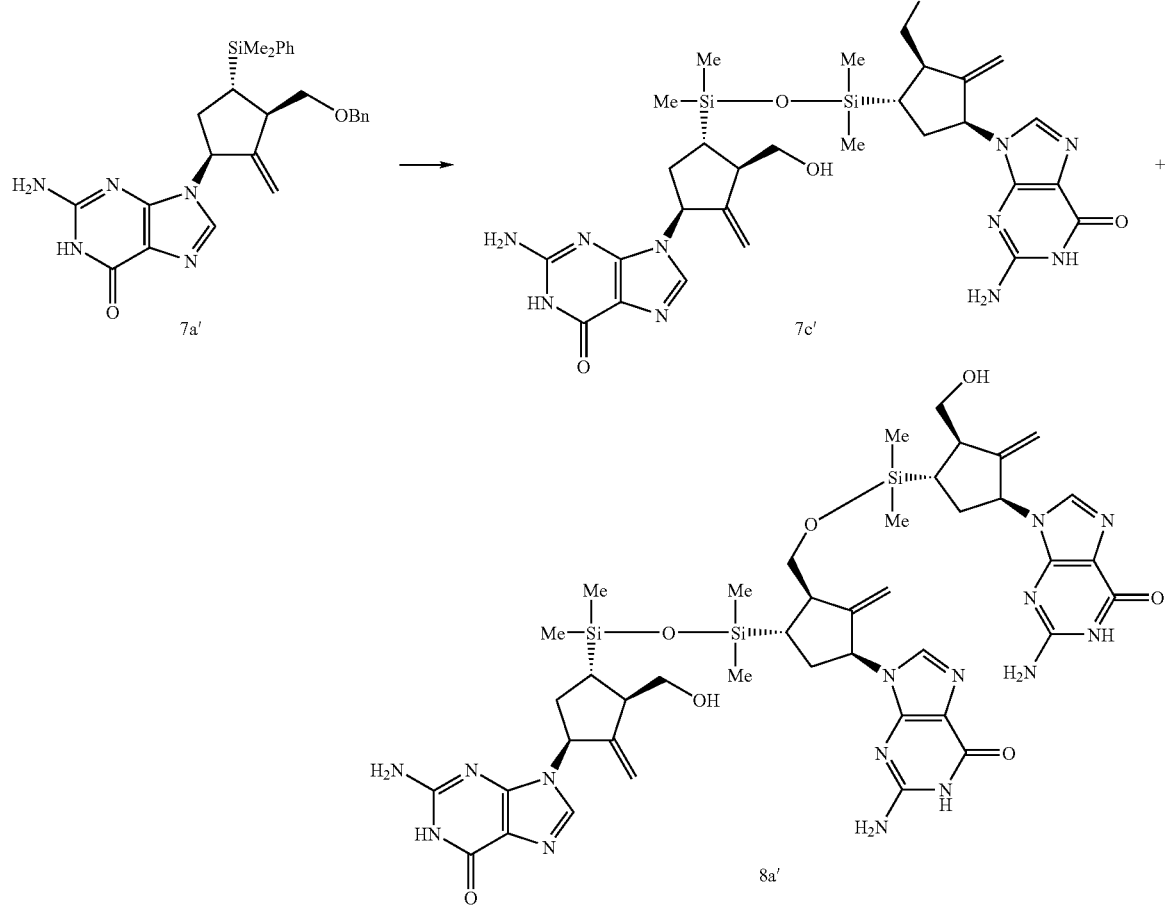

A dry 1-L 4-neck jacketed reactor with an overhead stirrer, a thermometer, an addition funnel and a $N_2$ inlet/outlet was charged with compound 7a' (30 g, 56.2 mmol) and DCM (100 mL) with agitation, and the reaction mixture was cooled to below 5° C. MSA (36.2 g, 376.6 mmol, 6.7 eq.) was slowly added to the reactor while maintaining the reactor temperature less than 15° C. $CF_3SO_3H$ (TFMSA, 16.5 mL, 182.7 mmol, 3.25 eq.) was then added slowly via the addition funnel while maintaining the reactor temperature below 5° C. The reaction mixture was allowed to warm to ambient temperature (21-25° C.) and continued to stir until reaction was complete as determined by HPLC. Triethylamine (87 mL, 623.9 mmol) was added to the reaction mixture slowly while maintaining the reactor temperature below 15° C. The resulting cloudy suspension was continued to stir at room temperature for about 5 hours. The suspension was cooled to 10° C.-15° C. and pre-mixed water (240 mL) and MeOH (480 mL) was added to the suspension while maintaining the temperature below 15° C. The resulting slurry was heated to about 28-30° C. and agitated for about 2-3 hours. The pH of the slurry was adjusted to 6.5 to 7.5 using glacial AcOH or TEA as required. The resulting mixture was heated to about 70° C. for about 1 hour and the distillate was removed. MeOH (100 mL) was charged to the reactor and distillation was resumed at about 80° C. until a final volume of 17-20 g/mL was reached. The resulting slurry was cooled to about 20 to 25° C. slowly and held at 17 to 22° C. for about 4 hours. The slurry was filtered collected, washed with DCM (2×100 mL), premixed MeOH (315 mL) and DI water (135 mL), MeOH (900 mL), and dried at 55 to 60° C. in a vacuum oven to give compound 7c' (17.88 g, 93.5%, may contain about 1% to about 20% of compound 8a'). LC/MS for 8a': retention time=20.1 min.; (M+H)=971. HPLC condition: run time=36 min.; flow rate=1 mL/min.; column temp.=25 deg. C; column=Inertsil ODS-2, 150×4.6 mm, 5 μm; wavelength=254 nm; Solvent A=$H_2O$; Solvent B=$CH_3CN$;

| Gradient:time (min.) | % A | % B |
| --- | --- | --- |
| 0 | 96 | 4 |
| 4 | 96 | 4 |
| 15 | 72 | 28 |
| 20 | 40 | 60 |
| 30 | 40 | 60 |
| 30.5 | 96 | 4 |
| 36 | 96 | 4 |

EXAMPLE 19

Preparation of Compound I (Entecavir)

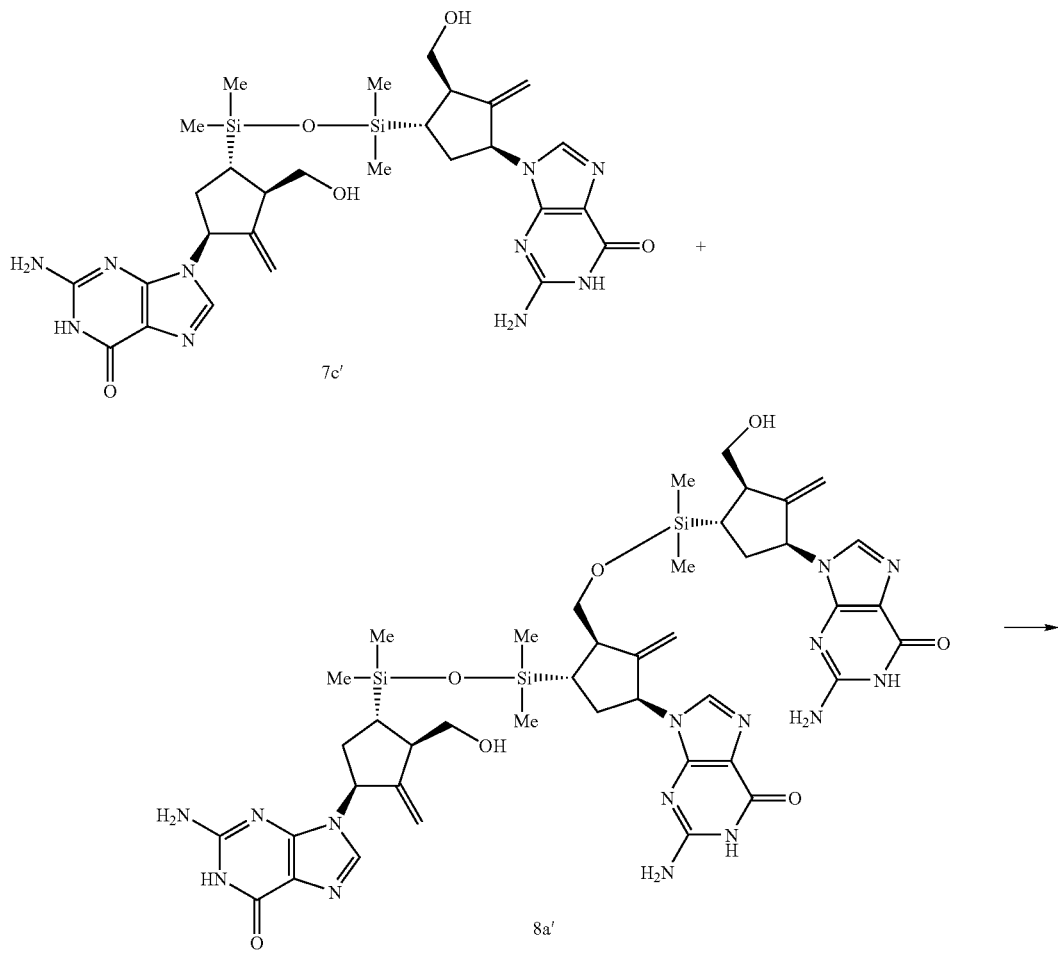

-continued

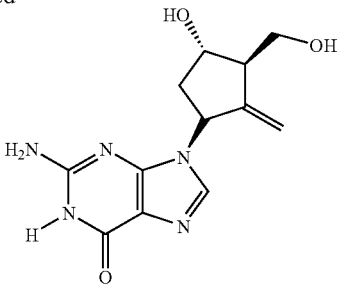

1 (entecavir)

A 500 mL 3-necked round bottom flask equipped with mechanical agitation, a condenser and a thermometer was charged with compound 7c' (15 g) (may contain about 1% to about 20% of compound 8a'), sodium carbonate peroxohydrate (13.2 g) and methanol (225 mL, 15 volumes) with agitation. The resulting mixture was heated to reflux and agitated until reaction was complete as determined by HPLC. The reaction mixture was then cooled to 20 to 25° C. and the resulting slurry was filtered through a filter paper and rinsed with methanol (5×50 mL). The filtrate was transferred to a 500 mL round-bottom flask equipped with a thermometer and a magnetic stirrer. Aqueous sodium thiosulfate was added (5×75 mL, 0.4M) and agitated until residual peroxide was quenched. The resulting slurry was concentrated under reduced pressure while maintaining the flask temperature at about 55° C. until a final volume of about 135 mL was achieved. The resulting mixture was heated to 70 to 75° C. to form a hazy solution/slurry, and 2N NaOH was added to adjust the pH of the solution to 10 to 11. The hazy solution/slurry was filtered through a filter paper while maintaining the temperature at about 55° C., and the filter cake was rinsed with warm water (3×45 mL, at 50 to 60° C.). The pH of the clear filtrate was adjusted to 6 to 7 at 70 to 75° C. using glacial acetic acid. The resulting mixture was heated to 90 to 95° C. for about 30 minutes and then cooled to room temperature slowly with agitation. The resulting slurry was filtered collected and washed with 2×50 mL cold water (5-10° C.), and dried under vacuum to give compound I (typical yield: 75 to 80%). Compound I may be further purified through decolorization upon treating with carbon and recrystallization from methanol, water, or a mixture thereof.

It is to be understood that the invention, as defined in the following claims, should not be restricted solely to the embodiments itemized herein.

We claim:

1. A process for the preparation of a compound of formula I,

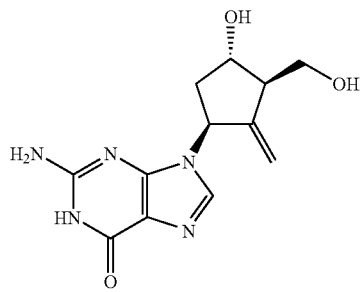

comprising:
(a) converting the compound of formula 3a to a compound of formula 3b via protodesilylation, wherein $R^a$ is allyl, phenyl, or phenyl substituted with one, two or three $C_1$-$C_4$ alkyl or $C_1$-$C_4$ alkoxy; each $R^b$ is independently $C_1$-$C_4$ alkyl; and $R^c$ is H or Bn,

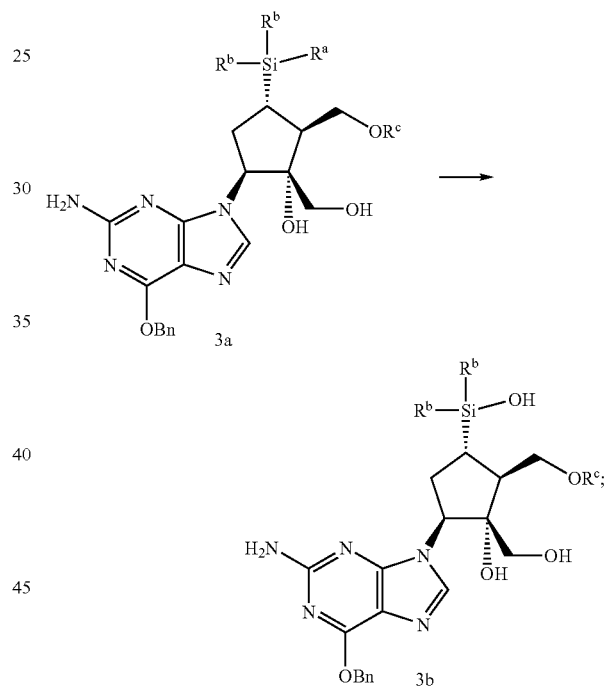

(b) further converting the compound of formula 3b to a compound of formula 3f,

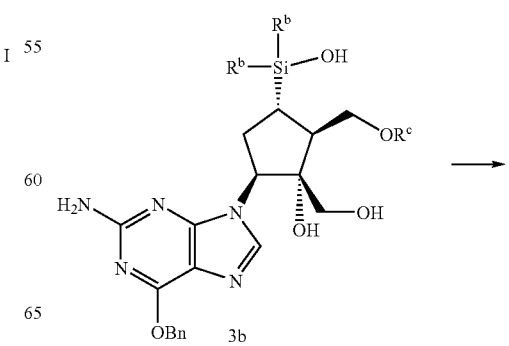

-continued

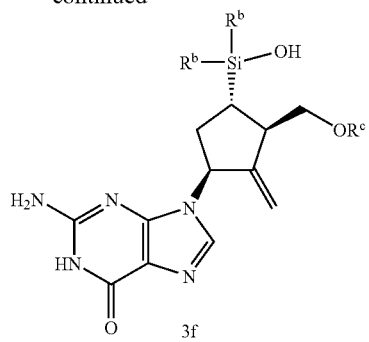

wherein each $R^b$ and $R^c$ are defined as hereinabove;
(c) oxidizing the compound of formula 3f to give the compound of formula I when $R^c$ is H; or a compound of formula 3 g when $R^c$ is Bn,

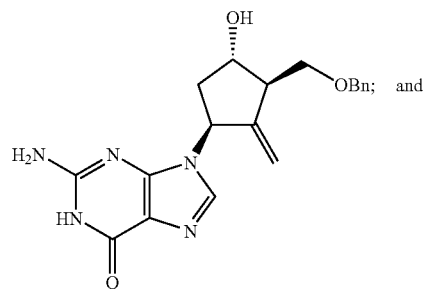

(d) deprotecting the benzyl group in the compound of formula 3g wherein $R^c$ is Bn to give a compound of I.

2. The process of claim 1, wherein step (b) comprises:

(i) reacting the compound of formula 3b with an orthoformate derivative, in the presence of a catalytic amount of an acid, or acid catalyst;

(ii) further reacting the resulting mixture from step (i) with an acid anhydride of formula $R^d$—C(=O)—O—C(=O)—$R^d$, wherein $R^d$ is $C_1$-$C_4$ alkyl; and optionally an acid of formula of $R^d$—C(=O)OH, wherein $R^d$ is $C_1$-$C_4$ alkyl; and further optionally in the presence of an antioxidant; and (iii) hydrolyzing the resulting compound from step (ii), with an aqueous mineral acid.

3. The process of claim 2, wherein $R^a$ is phenyl; each $R^b$ is methyl; and $R^d$ is methyl.

\* \* \* \* \*

UNITED STATES PATENT AND TRADEMARK OFFICE
CERTIFICATE OF CORRECTION

PATENT NO. : 7,511,139 B2
APPLICATION NO. : 11/143268
DATED : March 31, 2009
INVENTOR(S) : Maotang X. Zhou et al.

Page 1 of 1

It is certified that error appears in the above-identified patent and that said Letters Patent is hereby corrected as shown below:

Claim 1:
Column 45, line 19, change "3 g" to -- 3g --.

Signed and Sealed this
Fifth Day of April, 2011

David J. Kappos
*Director of the United States Patent and Trademark Office*